US009504744B2

(12) United States Patent
White et al.

(10) Patent No.: US 9,504,744 B2
(45) Date of Patent: *Nov. 29, 2016

(54) TREATMENT OF DIFFUSE LARGE-CELL LYMPHOMA WITH ANTI-CD20 ANTIBODY

(71) Applicant: BIOGEN INC., Cambridge, MA (US)

(72) Inventors: Christine A. White, Rancho Santa fe, CA (US); Antonio J. Grillo-Lopez, Rancho Santa Fe, CA (US)

(73) Assignee: Biogen Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/310,167

(22) Filed: Jun. 20, 2014

(65) Prior Publication Data

US 2014/0302018 A1 Oct. 9, 2014

Related U.S. Application Data

(60) Continuation of application No. 14/045,375, filed on Oct. 3, 2013, now Pat. No. 8,821,873, which is a division of application No. 09/628,187, filed on Jul. 28, 2000, now Pat. No. 8,557,244.

(60) Provisional application No. 60/148,286, filed on Aug. 11, 1999.

(51) Int. Cl.
A61K 39/395 (2006.01)
A61K 31/475 (2006.01)
A61K 31/573 (2006.01)
A61K 31/664 (2006.01)
A61K 31/704 (2006.01)
C07K 16/28 (2006.01)
A61K 31/675 (2006.01)
A61K 35/28 (2015.01)
A61K 35/545 (2015.01)
A61K 39/00 (2006.01)

(52) U.S. Cl.
CPC ......... A61K 39/3955 (2013.01); A61K 31/475 (2013.01); A61K 31/573 (2013.01); A61K 31/675 (2013.01); A61K 31/704 (2013.01); A61K 35/28 (2013.01); A61K 35/545 (2013.01); A61K 39/39558 (2013.01); C07K 16/2887 (2013.01); A61K 2039/505 (2013.01); C07K 2317/24 (2013.01); Y10S 424/801 (2013.01)

(58) Field of Classification Search
CPC .................. A61K 39/395; A61K 39/39533; A61K 39/39558; A61K 31/475; A61K 31/573; A61K 31/664; A61K 31/704; C07K 16/28; C07K 16/2803; C07K 16/2896; C07K 16/3061
See application file for complete search history.

(56) References Cited

U.S. PATENT DOCUMENTS

| 4,816,397 A | 3/1989 | Boss |
| 4,816,567 A | 3/1989 | Cabilly |
| 4,831,175 A | 5/1989 | Gansow et al. |
| 4,975,278 A | 12/1990 | Senter et al. |
| 5,099,069 A | 3/1992 | Gansow et al. |
| 5,124,471 A | 6/1992 | Gansow et al. |
| 5,145,677 A | 9/1992 | Von Eichborn et al. |
| 5,165,922 A | 11/1992 | Hellstrom et al. |
| 5,225,535 A | 7/1993 | DeFreitas et al. |
| 5,225,539 A | 7/1993 | Winter |
| 5,246,692 A | 9/1993 | Gansow et al. |
| 5,250,732 A | 10/1993 | Kogan et al. |
| 5,286,850 A | 2/1994 | Gansow et al. |
| 5,439,665 A | 8/1995 | Hansen et al. |
| 5,460,785 A | 10/1995 | Rhodes et al. |
| 5,500,362 A | 3/1996 | Robinson et al. |
| 5,530,101 A | 6/1996 | Queen et al. |
| 5,595,721 A | 1/1997 | Kaminski et al. |
| 5,633,425 A | 5/1997 | Lonberg et al. |
| 5,648,267 A | 7/1997 | Reff |
| 5,677,171 A | 10/1997 | Hudziak et al. |
| 5,677,180 A | 10/1997 | Robinson et al. |
| 5,686,072 A | 11/1997 | Uhr et al. |
| 5,691,135 A | 11/1997 | Braun et al. |
| 5,691,320 A | 11/1997 | Von Borstel et al. |
| 5,693,780 A | 12/1997 | Newman et al. |
| 5,721,108 A | 2/1998 | Robinson et al. |
| 5,726,023 A | 3/1998 | Cheever et al. |
| 5,736,137 A | 4/1998 | Anderson et al. |

(Continued)

FOREIGN PATENT DOCUMENTS

AU 56032/94 6/1994
EP 0 125 023 A1 11/1984

(Continued)

OTHER PUBLICATIONS

Arber, D.A., et al. Am. J. Surg. Pathol. 29: 1549-1557, 2005.*

(Continued)

Primary Examiner — Misook Yu
Assistant Examiner — Anne Holleran
(74) Attorney, Agent, or Firm — Wendy Lee; Ginger R. Dreger; Arnold & Porter LLP

(57) ABSTRACT

The present invention concerns methods for the treatment of diffuse large cell lymphoma by administration of an anti-CD20 antibody and chemotherapy. Particular embodiments include the administration of anti-CD20 antibody in combination with chemotherapy comprising CHOP (cyclophosphamide, hydroxydaunorubicin/doxorubicin, vincristine, and prednisone/prednisolone) and/or in combination with a transplantation regimen.

16 Claims, No Drawings

(56) References Cited

U.S. PATENT DOCUMENTS

| | | |
|---|---|---|
| 5,776,456 A | 7/1998 | Anderson et al. |
| 5,843,398 A | 12/1998 | Kaminski et al. |
| 5,843,439 A | 12/1998 | Anderson et al. |
| 6,015,542 A | 1/2000 | Kaminski et al. |
| 6,090,365 A | 7/2000 | Kaminski et al. |
| 6,111,166 A | 8/2000 | Van de Winkel |
| 6,120,767 A | 9/2000 | Robinson et al. |
| 6,183,744 B1 | 2/2001 | Goldenberg |
| 6,287,537 B1 | 9/2001 | Kaminski et al. |
| 6,306,393 B1 | 10/2001 | Goldenberg |
| 6,399,061 B1 | 6/2002 | Anderson et al. |
| 6,399,649 B1 | 6/2002 | Lerner |
| 6,455,043 B1 | 9/2002 | Grillo-Lopez |
| RE38,008 E | 2/2003 | Abrams |
| 6,565,827 B1 | 5/2003 | Kaminski et al. |
| 6,652,852 B1 | 11/2003 | Robinson et al. |
| 6,682,734 B1 | 1/2004 | Anderson et al. |
| 6,893,625 B1 | 5/2005 | Robinson et al. |
| 7,381,560 B2 | 6/2008 | Anderson et al. |
| 7,422,739 B2 | 9/2008 | Anderson et al. |
| 7,682,612 B1 | 3/2010 | White et al. |
| 7,744,877 B2 | 6/2010 | Anderson et al. |
| 8,206,711 B2 | 6/2012 | White et al. |
| 8,329,172 B2 | 12/2012 | Grillo-Lopez et al. |
| 8,557,244 B1 | 10/2013 | White et al. |
| 8,821,873 B2 | 9/2014 | White et al. |
| 2002/0009444 A1 | 1/2002 | Grillo-López |
| 2002/0197255 A1 | 12/2002 | Anderson et al. |
| 2003/0018014 A1 | 1/2003 | Lerner |
| 2003/0021781 A1 | 1/2003 | Anderson et al. |
| 2003/0026804 A1 | 2/2003 | Grillo-López |
| 2003/0082172 A1 | 5/2003 | Anderson et al. |
| 2003/0095963 A1 | 5/2003 | Anderson et al. |
| 2003/0147885 A1 | 8/2003 | Anderson et al. |
| 2003/0206903 A1 | 11/2003 | Grillo-López |
| 2004/0167319 A1 | 8/2004 | Teeling et al. |
| 2004/0213784 A1 | 10/2004 | Grillo-López |
| 2005/0163708 A1 | 7/2005 | Robinson et al. |
| 2005/0186205 A1 | 8/2005 | Anderson et al. |
| 2006/0034835 A1 | 2/2006 | Adams et al. |
| 2008/0038261 A1 | 2/2008 | Grillo-López |
| 2009/0074760 A1 | 3/2009 | Grillo-Lopez et al. |
| 2010/0080769 A1 | 4/2010 | Grillo-Lopez et al. |
| 2011/0165159 A1 | 7/2011 | Grillo-Lopez et al. |
| 2012/0251534 A1 | 10/2012 | Grillo-Lopez |
| 2012/0251535 A1 | 10/2012 | Grillo-Lopez |
| 2012/0258101 A1 | 10/2012 | Grillo-Lopez |
| 2012/0258102 A1 | 10/2012 | Grillo-Lopez |
| 2013/0273039 A1 | 10/2013 | Grillo-Lopez |
| 2013/0273041 A1 | 10/2013 | Grillo-Lopez et al. |
| 2014/0030263 A1 | 1/2014 | White et al. |
| 2014/0056887 A1 | 2/2014 | Grillo-Lopez |
| 2014/0302018 A1 | 10/2014 | White et al. |
| 2014/0363424 A1 | 12/2014 | Grillo-Lopez et al. |
| 2015/0183882 A1 | 7/2015 | Grillo-Lopez |

FOREIGN PATENT DOCUMENTS

| | | |
|---|---|---|
| EP | 0 173 494 A2 | 5/1986 |
| EP | 0 274 394 A2 | 7/1988 |
| EP | 0 274 394 A3 | 1/1990 |
| EP | 0 125 023 B1 | 6/1991 |
| EP | 0 510 949 A2 | 10/1992 |
| EP | 0 682 040 A1 | 11/1995 |
| EP | 0 451 216 B1 | 1/1996 |
| EP | 0 669 836 B1 | 3/1996 |
| EP | 0 752 248 A1 | 1/1997 |
| EP | 0 682 040 B1 | 8/1999 |
| EP | 0 125 023 B2 | 3/2002 |
| EP | 1974747 B1 | 6/2012 |
| JP | 5-508630 | 12/1993 |
| JP | H10-510526 | 6/1996 |
| MX | PA01001530 A | 2/2001 |
| WO | WO 87/02671 A1 | 5/1987 |
| WO | WO 88/04936 A1 | 7/1988 |
| WO | WO 89/00999 A1 | 2/1989 |
| WO | WO 91/04320 A1 | 4/1991 |
| WO | JP H5-508630 | 11/1991 |
| WO | WO 91/17770 | 11/1991 |
| WO | WO 92/07466 A1 | 5/1992 |
| WO | WO 93/02108 A1 | 2/1993 |
| WO | WO 94/08601 | 4/1994 |
| WO | WO 94/11007 | 5/1994 |
| WO | WO 94/11026 A2 | 5/1994 |
| WO | WO 96/018413 | 6/1996 |
| WO | WO 98/42378 | 10/1998 |
| WO | WO 00/09160 A1 | 2/2000 |
| WO | WO 00/27428 A1 | 5/2000 |
| WO | WO 00/27433 A1 | 5/2000 |
| WO | WO 01/10460 A1 | 2/2001 |
| WO | WO 2004/056312 A2 | 7/2004 |

OTHER PUBLICATIONS

Business of the Business: Concurrent Infusions, J. Oncology Practice, 4(4): 171, 2008.*

Meyer, R.M., et al., Leukemia and Lymphoma, 30: 591-600, Aug. 1998.*

Zinzani, et. al., "Elderly Aggressive-Histology Non-Hodgkin's Lymphoma: First-Line VNCOP-B Regimen Experience on 350 Patients", Blood, Jul. 1999, vol. 94, No. 1, pp. 33-38.

CancerNetwork, "Rituximab Effective in Patients with Bulky NHL", Feb. 1, 1999, www.cancernetwork.com/display/article/10165/86193, retrieved Feb. 23, 2011.

Cancer.Net, "Lymphoma—Non-Hodgkin", copyright 2005-2012, pp. 1-6; www.cancer.net/cancer-types/lymphoma-non-hodgkin/subtypes.

ClinicalTrials.gov, "Combination Chemotherapy With or Without Monoclonal Antibody Therapy in Treating Patients With Stage III or Stage IV Low-Grade Non-Hodgkin's Lymphoma", First Received: May 2, 2000; Last updated: Feb. 26, 2013; Last verified: Feb. 26, 2013 pp. 1-4; http://clinicaltrials.gov/show/NCT00003204.

Clinical Trials (PDQ®); "Phase III Randomized Study of Chop (Cyclophosphamide, Doxorubicin, Vincristine, and Prednisone) With or Without Rituximab in Older Patients With Diffuse Mixed, Diffuse Large, or Immunoblastic Large Cell Non-Hodgkin's Lymphoma" http://www.cancer.gov/clinicaltrials/search/view?cdrid=65935&version=HealthProfessional; First Published: Jan. 1, 1998; Last Modified: Aug. 27, 2010; Retrieved: Jan. 14, 2012; pp. 1-6.

Current Therapies and Future Directions in the Treatment of Non-Hodgkin's Lymphoma, Classification of Lymphoma, [Retrieved on Feb. 25, 2003], Retrieved from the Internet<http://onsopcontent.ons.org/oes/online_ce/lymph/.05-classification.htm.

"Dictionary of Cancer Terms", National Cancer Institute at the National Institutes of Health, http://www.cancergov.dictionary?CdrID=45735, 1 pp, printed May 22, 2012.

ECOG's Active Protocols: ECOG Protocols Active as of May 19, 1998, 1 page, Internet Archive, Wayback Machine, http://web.archive.org/web/19980519084342/http://ecog.dfci.harvard.edu/~ecogdba/active_reports/Lymphoma.html.

ECOG E1496 Trial Results "Non-Progressing Low-grade NHL after CVP—Rituxan® (Rituximab)", pp. 1-7, printed on Dec. 2, 2010.

FDA label of Doxorubicin Hydrochloride for injection USP, pp. 1-22, 2010.

Rituxan® Rituximab Prescribing Information, Initial US Approval; 1997, Revised Sep. 2013. (pp. 1-41).

Rituxan® (Rituximab) ECOG 1496 Trial for Low-grade or Follicular Non-Hodgkin's Lymphoma, 2012, pp. 1-3, http://www.rituxan.com/hem/hcp/non-hodgkin/post-induction/ecog/index.html.

Rituxan (Rituximab) full prescribing information, pp. 1-2 (Nov. 1997).

2010 Full prescribing information for Rituxan (rituximab). (Revised Feb. 2010) pp. 1-35.

2011 Rttuxan (Rituximab) full prescribing information (Revised Jan. 2011) pp. 1-8.

(56) References Cited

OTHER PUBLICATIONS

2012 Rituxan (Rituximab) full prescribing information (Revised Oct. 2012) pp. 1-40.
[unknown author] "IDEC Pharmaceuticals Announces Positive Preliminary Results for Pivotal Trial of TDEC-C2B8" The Free Library May 21, 1996. [retrieved again on Aug. 2, 2010]. Retrieved from http://www.thefreelibrary.com/IDEC+PHARMACEUTICALS+ANNOUNCES+POSITIVE+PRELIMINARY+RESULTS+FOR . . . -a018307934.
[unknown author} "Non-progressing, low-grade NHL: Risk reduction demonstrated in NCI-sponsored trial using up to 16 doses of Rituxan following CVP in NHL" [retrieved on Aug. 25, 2010. Retrieved from http://www.rituxan.com/lymphoma/hcp/indications/E1496/index.m.
"National Cancer Institute sponsored study of classifications of non-Hodgkin's lymphomas: summary and description of a working formulation for clinical usage," Cancer, 1982, vol. 49, pp. 2112-2135.
Non-Hodgkin's Lymphoma Pathologic Classification Project. Cancer 49(10): 2112-35, 1982. National Cancer Institute sponsored study of classifications of non-Hodgkin's lymphomas.
"GlaxoSmithKline and Genmab Announce Results from a Study of Arzerra in Rituximab Refractory Follicular NHL," Phar maLive. Com, pp. 1-2, Aug. 17, 2009. Obtained online at http://www.pharmalive.com/News/Print.cfm?articleid=645905. Retrieved on Aug. 21, 1999.
MabThera® Summary of Product Characteristics; Date of first authorization: Jun. 2, 1998; Date of latest renewal: Jun. 2, 2008, pp. 1-94.
Chemocare.com, "Oncovin" 2013, pp. 1-6; www.chemocare.com/chemotherapy/drug-info/Oncovin.aspx.
Roche press release, Investor Update, Basel, Jun. 7, 2004, MabThera/Rituxan® maintenance therapy dramatically improves progression-free survival in patients with indolent Non-Hodgkin's Lymphoma (NHL), pp. 1-3.
Thompson Reuters Pharma™ "Drug Report: Rituximab", 2011, pp. 1-4.
Adams R.A. *Cancer Res.* 27: 2479-82, 1967. "Formal discussion: the role of transplantation in the experimental investigation of human leukemia and lymphoma."
Adams R.A. et al. *Cancer Res.* 28(6): 1121-25, 1968. "Direct implantation and serial transplantation of human acute lymphoblastic leukemia in hamsters, SB-2."
Alas S. et al. *Anticancer Res.* 20(5A): 2961-66, 2000. "Potentiation of fludarabine cytotoxicity on non-Hodgkin's lymphoma by pentoxifylline and rituximab."
Alas S. et al. *Clin. Cancer Res.* 7(3): 709-23, 2001. "Inhibition of interleukin 10 by rituximab results in down-regulation of bcl-2 and sensitization of B-cell non-Hodgkin's lymphoma to apoptosis."
Alas S. et al. *Clin. Cancer Res.* 8(3): 836-45, 2002. "Rituximab modifies the cisplatin-mitochondrial signaling pathway, resulting in apoptosis in cisplatin-resistant non-Hodgkin's lymphoma."
Almasri N.M. et al. *Am. J. Hematol.* 40: 259-63, 1992. "Reduced expression of CD20 antigen as a characteristic marker for chronic lymphocytic leukemia."
Amit A.G. et al., *Science* 233(4765): 747-53 (1986) "Three-dimensional structure of an antigen-antibody complex at 2.8 Å resolution,".
Anderson D.R. et al. *Biochem. Soc. Trans.* 25(2): 705-08, 1997. "Targeted anti-cancer therapy using rituximab, a chimaeric anti-CD20 antibody (IDEC-C2B8) in the treatment of non-Hodgkin's B-cell lymphoma."
Anderson D.R. et al. *Second IBC Int'l. Conference on Antibody Engineering*, San Diego, Dec. 16-18, 1991 "Immunoreactivity and effector function associated with a chimeric anti-CD20 antibody (abstract of presentation)."
Anderson K.C. et al. *Blood* 63(6): 1424-33, 1984. "Expression of human B cell-associated antigens on leukemias and lymphomas: a model of human B cell differentiation."

Anderson K.C. et al. *Blood* 69(2): 597-604, 1987. "Hematologic engraftment and immune reconstitution posttransplantation with anti-B 1 purged autologous bone marrow."
Appelbaum F.R. Hem. *One. Clin. N Amer.* 5(5): 1013-25, 1991. "Radiolabeled monoclonal antibodies in the treatment of non-Hodgkin's lymphoma."
Arico et al., *Arch Dis Child* 66, 1991, pp. 985-986. "Long term survival after heart transplantation for doxorubicin induced cardiomyopathy".
Armitage J.O., *N. Engl. J. Med.* 328(14): 1023-30 (Apr. 1993) "Treatment of Non-Hodgkin's Lymphoma."
Armitage J.O. et al. *Cancer* 50: 1695-1702, 1982. "Predicting therapeutic outcome in patients with diffuse histiocytic lymphoma treated with cyclophosphamide, adriamycin, vincristine and prednisone (CHOP)."
Armitage J.O. et al. *J. Clin. Oncol.* 16(8): 2780-95, 1998. "New approach to classifying non-Hodgkin's lymphomas: clinical features of the major histologic subtypes. Non-Hodgkin's Lymphoma Classification Project."
Arranz R. et al. *J. Clin. Oncol.* 16(4): 1538-46, 1998. "Role of interferon alfa-2b in the induction and maintenance treatment of low-grade non-Hodgkin's lymphoma: results from a prospective, multicenter trial with double randomization."
Azogui O. et al. *J. Immunol.* 131: 1205-08, 1983. "Inhibition of IL-2 production after human allogeneic bone marrow transplantation."
Badger C.C. et al. *Cancer Res.* 46: 6223-28, 1986. "Experimental radioimmunotherapy of murine lymphoma with $^{131}$I-labeled anti-T-cell antibodies."
Belhadj K. et al. *Ann. Oncol.* 15: 504-10, 2004. "Efficiency of in vivo purging with rituximab prior to autologous peripheral blood progenitor cell transplantation in B-cell non-Hodgkin's lymphoma: a single institution study."
Bentley, M. and Taylor, K., *Australian and New Zealand Journal of Medicine* 27, 1997, pp. 150-155 "Low-grade non-Hodgkin's lymphoma—Biology and therapeutic approaches".
Berinstein N. et al. *Proc. Amer. Assn. Cancer Res.* 38: 85, abst. No. 567, Mar. 1997. "IDEC-C2B8.(rituximab) levels correlate with response in low-grade or follicular non-Hodgkin's lymphoma (LG-F-NHL)."
Berinstein N.L. et al. *Ann. Oncol.* 9: 995-1001, 1998. "Association of serum rituximab (IDEC-C2B8) concentration and anti-tumor response in the treatment of recurrent low-grade or follicular non-Hodgkin's lymphoma."
Berinstein, *Leukemia Res.* 30 Suppl. 1: S3-10 (2006) "Principles of maintenance therapy,".
Berkahn et al., *J. Hematother.* Stem Cell Res. 11(2): 315-20 (2002) "In vivo purging with rituximab prior to collection of stem cells for autologous transplantation in chronic lymphocytic leukemia".
Beychok S. (in) Cells of Immunoglobulin Synthesis, B. Perris et al., eds. New York: Academic Press, 1979, pp. 69-88. "Comparative aspects of in vitro and cellular assembly of immunoglobulins."
Bhan A.K. et al. *J. Exp. Med.* 154: 737-49, 1981. "Stages of B cell differentiation in human lymphoid tissue."
Bierman P.J. et al. (in) Hoffinan, R., ed., Hematology, 2d. ed., Churchill Livingstone, 1995, Chapter 81, pp. 1278-1298. "Clinical manifestations and staging of and therapy for non-Hodgkin's lymphomas."
Bierman et al., *J. Clin. Oncol.* 15(2):445-50 (1997) "High-dose therapy with autologous hematopoietic rescue for follicular low-grade non-Hodgkin's lymphoma".
*Biogen Idec Inc.* v. *Corixa Corp.*, Case No. 01-CV-1637 IEG [Doc. Nos. 635, 552, 486] (S.D. Cal. Jan. 22, 2004).
*Biogen Idec Inc.* v. *Corixa Corp.*, Case No. 01-CV-1637 IEG (RBB), Order Granting Patentees' Motion for Reconsideration, etc. (S.D.Cal., Jan. 22, 2004).
*Biogen Idec Inc.* v. *Corixa Corp.*, Case No. 01-CV-1637 IEG (RBB), Stipulation of Dismissal of Claims and Counterclaims with Prejudice and Order (S.D.Cal., May 13, 2004).
Bodkin et al., *Proc Annu Meet Am Assoc Cancer Res* 36:365 (#2175), Mar. 1995 "Pharmacokinetic analysis of serum concentrations of the chimeric anti-CD20 antibody IDEC-C2B8 in patients with relapsed B cell lymphoma".

(56) References Cited

OTHER PUBLICATIONS

Boon, *Adv. Cancer Res.* 58: 177-210 (1992) "Toward a genetic analysis of tumor rejection antigens".

Bosly A. et al. *Nouv. Rev. Fr. Hematol.* 32(1): 13-16, 1990. "Interleukin-2 after autologous bone marrow transplantation as consolidative immunotherapy against minimal residual disease."

Boulianne G.L. et al., *Nature* 312: 643-46, 1984. "Production of functional chimaeric mouse/human antibody."

Brown et al., *Blood* 73:651-661, 1989 "Treatment of B-cell lymphomas with anti-idiotype antibodies alone and in combination with alpha interferon".

Brunner K.T. et al., *Immunology* 14(2): 181-96, 1968. "Quantitative assay of the lytic action of immune lymphoid cells on Cr-labelled allogeneic target cells in vitro; inhibition by isoantibody and by drugs."

Buchsbaum D.J. et al., *Cancer Res.* 50: 993s-999s, 1990. "Comparative binding and preclinical localization and therapy studies with radiolabeled human chimeric and murine 17-1A monoclonal antibodies."

Buchsbaum D.J. et al., *Cancer Res.* 52: 637-642, 1992. "Improved delivery of radiolabeled anti-B1 monoclonal antibody to Raji lymphoma xenografts by predosing with unlabeled anti-B1 monoclonal antibody."

Buchsbaum D.J. et al., *Cancer Res.* 52: 6476-81, 1992. "Therapy with unlabeled and $^{131}$I-labeled pan-B-cell monoclonal antibodies in nude mice bearing Raji Burkitt's lymphoma xenografts."

Buchsbaum D.J. et al., *I.J. Rad. Oncol. Biol. Phys.* 18: 1033-41, 1990. "A comparison of $^{131}$I-labeled monoclonal antibody 17-1A treatment to external beam irradiation on the growth of LS174T human colon carcinoma xenografts."

Buchsbaum D.J. et al., *I. J. Rad. Oncol. Biol. Phys.* 25(4): 629-38, 1993. "Comparison of $^{131}$I-and $^{90}$Y-labeled monoclonal antibody 17-1A for treatment of human colon cancer xenografts."

Buske et al., *European Journal of Cancer*, vol. 35(4), 1999, pp. 549-557, "Monoclonal Antibody Therapy for B Cell Non-Hodgkin's Lymphomas: Emerging Concepts of a Tumour-targeted Strategy".

Byrd J.C., *Cancer Biother. Radiopharm.* 14(4)L 323, 1999. "Rituximab therapy in patients with chronic lymphocytic leukemia."

Byrd et al., "Old and New therapies in Chronic Lumphocytic Leukemia: Now Is the Time for a Reassessment of Therapeutic Goals", Seminars in Oncology, vol. 25, No. Feb. 1, 1998; pp. 65-74.

Byrd J.C. et al., *Blood* 92(10 Suppl. 1): 106a, abst. No. 432 Nov. 1998. "Rituximab therapy in hematologic malignancy patients with circulating blood tumor cells: association with increased infusion-related side effects and rapid tumor lysis."

Byrd J.C. et al., *Blood* 92(10 Suppl. 1): 106a, abst. No. 433 Nov. 1998. "Rituximab therapy in previously treated Waldenstrom's Macroglobulinemia: Preliminary evidence of activity."

Byrd J.C. et al., *J. Clin. Oncol.* 17(3): 791-795, Mar. 1999. "Rituximab therapy in hematologic malignancy patients with circulating blood tumor cells: association with increased infusion-related side effects and rapid blood tumor clearance."

Byrd J.C. et al., *J. Clin. Oncol.* 19(8): 2153-64, 2001. "Rituximab using a thrice weekly dosing schedule in B-cell chronic lymphocytic leukemia and small lymphocytic lymphoma demonstrates clinical activity and acceptable toxicity."

Cabanillas, F. et al., *Blood* 88(10):91a (#351), Nov. 1996 "Anti-CD20 Antibody (MAB), IDEC-C2B8: Clearance of BCL-2 t(14;18) positive cells from peripheral blood (PB) and bone marrow (BM) in patients (PTS) with relapsed low-grade or follicular lymphoma (LG/F NHL)".

Caligiuri, M.A. *Semin. Oncol.* 20(6 Suppl 9): 3-10, 1993. Low-dose interleukin-2 therapy: rationale and potential clinical applications.

Caligiuri M.A. et al. *J. Clin. Invest.* 91(1): 123-32, 1993. Selective modulation of human natural killer cells in vivo after prolonged infusion of low dose recombinant interleukin 2.

Caligiuri M.A. et al. *J. Clin. Oncol.* 9(12): 2110-19, 1991. "Extended continuous infusion low-dose recombinant interleukin-2 in advanced cancer: prolonged immunomodulation without significant toxicity."

Calvert J.E. et al. *Semin. Hematol.* 21(4): 226-243, 1984. "Cellular events in the differentiation of antibody-secreting cells."

Carrasquillo J.A. et al. *J. Nucl Med.* 26: 67, abst. No. 276, 1985. "Improved imaging of metastatic melanoma with high dose 9.2.27 In-111 monoclonal antibody."

Catovsky D. et al. *Eur J. Cancer* 31A(13/14): 2146-54, 1995. "Key issues in the treatment of chronic lymphocytic leukaemia (CLL)."

Cayeux S. et al. *Blood* 74(6): 2270-77, 1989. "T-cell ontogeny after autologous bone marrow transplantation: failure to synthesize interleukin-2 (IL-2) and lack of CD2– and CD3– mediated proliferation by both CD4– and CD8+ cells even in the presence of exogenous IL-2."

Chen J.J. et al. *J. Immunol.* 143(3): 1053-57, 1989. "Tumor idiotype vaccines. VI. Synergistic anti-tumor effects with combined "internal image" anti-idiotypes and chemotherapy."

Cheson B.D. et al. *Blood* 87: 4990-97, 1996. National Cancer Institute-specified working group guidelines for chronic lymphocytic leukemia: revised guidelines for diagnosis and treatment.

Cheson, B. et al., *J Clin Oncol* 17(4):1244-53, Apr. 1999 "Report of an International Workshop to Standardize Response Criteria for Non-Hodgkin's Lymphomas".

Cheson, *Blood* 101(2): 391-8 (2003), Epub Sep. 19, 2002 "Radioimmunotherapy of non-Hodgkin lymphomas."

Chinn P. et al. *Proc. Ann. Mtg. Am. Assn. Cancer Res.* 33: 337, abst. No. 2012, 1992. "Production and characterization of radiolabeled anti-CD20 monoclonal antibody: potential application to treatment of B-cell lymphoma."

Chinn P.C et al. *Int. J. Oncol.* 15(5): 1017-25, Nov. 1999. "Preclinical evaluation of 90Y-labeled anti-CD20 monoclonal antibody for treatment of non-Hodgkin's lymphoma."

Chinn P.C et al. *Proc. Am. Assn. Cancer Res.* 40: 574, abst. No. 3786, 1999, "A $^{90}$Y-labeled anti-CD20 monoclonal antibody conjugated to MX-DTPA, a high-affinity chelator for yttrium."

Chomczynki P. et al. *Anal. Biochem.* 162: 156-59, 1987, "Single-step method of RNA isolation by acid guanidinium thiocyanate-phenol-chloroform extraction."

Chow K.U. et al. *Haematologica* 87: 33-43, 2002, "Anti-CD20 antibody (IDEC-C2B8, rituximab) enhances efficacy of cytotoxic drugs on neoplastic lymphocytes in vitro: role of cytokines, complement, and caspases."

Clark E.A. et al. *J. Cell. Biochem.* (Suppl. 9A): 63, 1985, "Anti-Bp35 antibody induces human B cell proliferation: implications for in vivo immunotherapy."

Clark E.A. et al. *Proc. Nat'l Acad. Sci. USA* 82(6): 1766-70, 1985, "Role of the Bp35 cell surface polypeptide in human B-cell activation."

Classon B.J. et al. *J. Exp. Med.* 169(4): 1497-1502, 1989, "The primary structure of the human leukocyte antigen CD37, a species homologue of the rat MRC OC-44 antigen."

Cogliatti S.B. et al. *Sw. Med. Weekly* 192: 607-17, 2002. Who is Who and what was Real.

Cohen Y. et al. *Leuk. Lymphoma* 43(7): 1485-87, 2002, "Large B-cell lymphoma manifesting as an invasive cardiac mass: sustained local remission after combination of methotrexate and rituximab."

Cohen et al., *Hematol. J.* 4(2): 151-3 (2003) "Retreatment with rituximab alone induces sustained remission in a patient with follicular lymphoma with multiple extranodal sites of involvement, relapsing soon after primary treatment with fludarabine-rituximab."

Coiffier, *Semin. Oncol.* 29(2 Suppl. 6): 18-22 (2002), "Rituximab in combination with CHOP improves survival in elderly patients with aggressive non-Hodgkin's lymphoma".

Coiffier B., *Ann. Oncol.* 83(Suppl 1): S73-S74, 2004, "New treatment strategies in lymphomas: aggressive lymphomas."

Coiffier B. et al., *Blood* 92(6): 1927-32, 1998, "Rituximab (anti-CD20 monoclonal antibody) for the treatment of patients with relapsing or refractory aggressive lymphoma: a multicenter phase II study."

(56) References Cited

OTHER PUBLICATIONS

Coiffier B. et al., *N. Engl. J. Med.* 346(4): 235-42, 2002, "CHOP chemotherapy plus rituximab compared with CHOP alone in elderly patients with diffuse large-B-cell lymphoma."

Coleman M. et al., *Blood* 102(11 pt.1): 29a, abst. No. 29, 2003, "The Bexxar® therapeutic regimen (tositumomab and Iodine 1-131 tositumomab) produced durable complete remissions in heavily pretreated patients with non-Hodgkin's lymphoma (NHL), rituximab-relapsed/ refractory disease, and rituximab-I disease."

Colombat P. et al., *Blood* 97: 101-06, 2001, "Rituximab (anti-CD20 monoclonal antibody) as single first-line therapy for patients with follicular lymphoma with a low tumor burden: clinical and molecular evaluation."

Comella, et al., *Tumori*, vol. 68, No. 2, pp. 137-142, (1982), "Combination chemotherapy (CVP or CHOP)-radiotherapy approach in early stage non-Hodgkins's lymphomas".

Cope, *Oncology* 8(4): 100, 1994, "Antibody shows promise in treating B-cell lymphoma."

Curti B.D., *Crit. Rev. Oncol. Hematol.* 14(1): 29-39, 1993. "Physical barriers to drug delivery in tumors."

Czuczman M.S. et al., *Blood* 94(10 Supp. 1): 99a, abst. No. 432, 1999. Rituximab/CHOP chemoimmunotherapy in patients (PTS) with low grade lymphoma (LG/F NHL): progression free survival (PFS) after three years (median) follow-up.

Czuczman M.S. et al., *J. Clin. Oncol.* 17(1): 268-76, Jan. 1999. "Treatment of patients with low-grade B-cell lymphoma with the combination of chimeric anti-CD20 monoclonal antibody and Chop chemotherapy."

Czuczman M.S. et al., *Cancer Investigation* (abstract 53) 14(Suppl. 1):59-61 "Chemoimmunotherapy of Low-Grade Lymphoma with the Anti-CD20 Antibody IDEC-C2B8 in Combination with Chop Chemotherapy", (1996).

Czuczman M.S. et al., *Annals of Oncology*, vol. 7, Suppl. 1, pp. 56-57 "IDEC-C2B8/CHOP chemoimmunotherapy in patients with low-grade lymphoma: Interim clinical and bc1-2 (PCR) results", (1996).

Czuczman M.S. et al., *J. Mol. Med.* 75(7): B231, abstract #258, "IDEC-C2B8/CHOP chemoimmunotherapy in patients with low grade lymphoma: Clinical and bcl-2 (PCR) results," (1997).

Czuczman et al., *Cancer Invest* 16 (1 Suppl):21-22 (#17), "IDEC-C2B8 (Rituximab) alone and in combination with CHOP in the treatment of low-grade B-cell lymphoma", 1998.

Czuczman et al., *Blood* 86(10 suppl 1):55a (#206), "IDEC-C2B8 and CHOP chemoimmunotherapy of low-grade lymphoma", Nov. 1995.

Czuczman et al., *J Immunother* 20 (5):401, Sep. 1997, "Rituxan™/ CHOP Chemo immunotherapy in patients with low-grade or follicular (LG/F) non-Hodgkin's lymphoma (NHL)".

Czuczman et al., *Ann Oncol* 7 (5 Suppl):111 (#532P), "The Anti-CD20 Antibody (MAB) IDEC-C2B8 Clears Lymphoma Cells Bearing the t(14;18) Translocation (bcl-2) from the Peripheral Blood (PB) and Bone Marrow (BM) of a Proportion of Patients (PTS) with Low-Grade or Follicular (LG/F) Non-Hodgkin's Lymphoma (NHL)", Nov. 1996.

Czuczman et al., *Proc. Annu. Meeting Amer. Assn. Cancer Res* 38:84 (#565), Mar. 1997, "IDEC-C2B8 clears bcl-2 (t14;18) in patients (pts) with relapsed low grade or follicular lymphoma (LG/F NHL)".

Czuczman et al., *Proc Am Soc Clin Oncol* 14:401 (#1261), Mar. 1995, "Phase II Clinical Trial of IDEC-C2B8/CHOP Combination Therapy in Low Grade Lymphoma: Preliminary Results".

Czuczman et al., *Blood* 88(10):453a (#1799), Nov. 1996, "IDEC-C2B8/CHOP Chemoimmunotherapy in Patients with Low-Grade Lymphoma: Clinical BCL-2 (PCR) Final Results".

Dallaire et al., *J Mol Med* 75 (7):B230-B231 (#256), "IDEC-C2B8 (Rituximab): Biology and preclinical studies", Jul. 1997.

Dana et al., *J. Clinical Oncology*, vol. 11, No. 4 (Apr. 1993), pp. 644-651, "Long-Term Follow-Up of Patients With Low-Grade Malignant Lymphomas Treated With Doxorubicin-Based Chemotherapy or Chemoimmunotherapy".

Davis T.A. et al., *J. Clin. Oncol.* 18: 3135-3143 (2000), "Rituximab Anti-CD20 Monoclonal Antibody Therapy in Non-Hodgkin's Lymphoma: Safety and Efficacy of Re-Treatment".

Davis T.A. et al., *Blood* 90(10 Suppl. 1): 509a, abst No. 2269, Nov. 1997, "Retreatments with Rituxan™ (Rituximab, Idec-C2B8) have significant efficacy, do not cause HAMA, and are a viable minimally toxic alternative in relapsed or refractory non-Hodgkin's lymphoma (NHL)."

Davis T.A. et al., *Proc. Amer. Soc. Clin. Oncol.* 17: abst. No. 39, May 1998, "Combination immunotherapy of low grade or follicular (LG/F) non-Hodgkin's lymphoma (NHL) with rituximab and alpha interferon: interim analysis."

Davis T.A. et al., *Blood* 86(10 Suppl. 1): 273a, abst. No. 1080, 1995, "$^{90}$Yttrium labeled anti-CD20 therapy for recurrent B cell lymphoma."

Davis T.A. et al., *Blood* 92(10 Suppl. 1): 414a, abst. No. 1710, Nov. 1998, "Rituximab: phase II (PII) retreatment (ReRx) study in patients (PTS) with low grade or follicular (LG/F) NHL."

Davis T.A. et al., *Blood* 92(10 Suppl. 1): 414a, abst. No. 1711, Nov. 1998, "Rituximab: first report of a phase II (PII) trial in NHL patients (PTS) with bulky disease."

Davis T.A. et al. *Clin. Cancer Res.* 5(3): 611-15, 1999, "Therapy of B-cell lymphoma with anti-CD20 antibodies can result in the loss of CD20 antigen expression."

Davis T.A. et al., *J. Clin. Oncol.* 17(6): 1851-57, 1999, "Single-agent monoclonal antibody efficacy in bulky non-Hodgkin's lymphoma: results of a phase II trial of rituximab."

Davis T.A. et al., *Proc. Amer. Assn. Cancer Res.* 39: 435, abst. No. 2964, 1998, "Therapy of B cell lymphoma with anti-CD20 can result in relapse with loss of CD20 expression."

Davis et al., *Blood*, vol. 92, No. 4 (Aug. 15, 1998): pp. 1184-1190, "Anti-Idiotype Antibodies Can Induce Long-Term Complete Remissions in Non-Hodgkin's Lymphoma Without Eradicating the Malignant Clone".

Demidem A. et al., *FASEB J* 9(3):A206, Abstract #1197, 1995, "Chimeric anti-CD20 antibody (IDEC-C2B8) is apoptotic and sensitizes drug resistant human B cell lymphomas and AIDS related lymphomas to the cytotoxic effect of CDDP, VP-16 and toxins".

Demidem A. et al., *Cancer Biother. Radiopharm.* 12(3): 177-86, 1997, "Chimeric anti-CD20 (IDEC-C2B8) monoclonal antibody sensitizes a B cell lymphoma cell line to cell killing by cytotoxic drugs."

DeNardo G.L. et al., *Cancer Res.* 50(3 Suppl.): 1014s-1016s, 1990, "Fractionated radioimmunotherapy of B-cell malignancies with $^{131}$I-Lym-1."

DeNardo G.L. et al., *I.J. Rad. Oncol. Biol. Phys.* 11(2): 335-48, 1985, "Requirements for a treatment plan in system for radioimmunotherapy."

DeNardo S.J. et al., *Antibody Immunoconj. Radiopharm.* 1(1): 17-33, 1988, "Pilot studies of radioimmunotherapy of B cell lymphoma and leukemia using I-131 Lym-1 monoclonal antibody."

DeNardo S.J. et al., *Cancer* 73(3 Suppl.): 1023-32, 1994, "The biologic window for chimeric L6 radioimmunotherapy."

Di Gaetano N. et al., *Br. J. Haematol.* 114(4): 800-09, 2001, "Synergism between fludarabine and rituximab revealed in a follicular lymphoma cell line resistant to the cytotoxic activity of either drug alone."

Dickson S., *Gen. Engr. News* 5(3): Mar. 1, 1985, "Scientists produce chimeric monoclonal Abs."

Dillman R.O., *J. Clin. Oncol.* 12(7): 1497-1515, 1994, "Antibodies as cytotoxic therapy."

Eary J.F. et al., *J Nucl. Med.* 31(8): 1257-68, 1990, "Imaging and treatment of B-cell lymphoma."

Einfeld D.A. et al., *EMBO J.* 7: 711-17, 1988, "Molecular cloning of the human B cell CD20 receptor predicts a hydrophobic protein with multiple transmembrane domains."

Eisenbeis C.F. et al., *Clin. Cancer Res.* 10: 6101-10, 2004, "Combination immunotherapy of B-cell non-Hodgkin's lymphoma with rituximab and interleukin-2: a preclinical and phase I study."

Endo K., *Jpn. J. Cancer Chemother.* 26: 744-48, 1999, "Current status of nuclear medicine in Japan."

Engert A. et al., *Ann. Hematol.* 77(suppl. 2): S180, abst. No. 717, 1998, "Multicenter phase II study of the monoclonal anti-CD20

(56) References Cited

OTHER PUBLICATIONS antibody rituximab (IDEC-C2B8) in patients with intermediate/high grade non-Hodgkin's lymphoma."

Feugier et al., *Journal of Clinical Oncology*, vol. 23, No. 18, Jun. 20, 2005, pp. 4117-4126, "Long-Term Results of the R-CHOP Study in the Treatment of Elderly Patients With Diffuse Large B-Cell Lymphoma: A Study by the Groupe d'Etude des Lymphomes de l'Adult".

Fisher D.C. et al., *Blood* 92: 247a, abst. No. 1010, 1998, "Phase 1 trial with CD40-activated follicular lymphoma cells: a novel cellular vaccine strategy for B cell malignancies."

Flinn I.W. et al., *Blood* 92(10 Suppl. 1): 648a, abst. No. 2678, Nov. 1998, "In vivo purging and adjuvant immunotherapy with rituximab during PBSC transplant for NHM [sic]."

Flinn et al., *Biol Blood Marrow Transplant*. 2000; 6 (6): pp. 628-632, "Immunotherapy with rituximab during peripheral blood stem cell transplantation for non-Hodgkin's lymphoma."

Foon K.A., *Curr. Probl. Cancer* 13(2): 57-128 (Mar./Apr. 1989), "Laboratory and Clinical Applications of Monoclonal Antibodies for Leukemias and Non-Hodgkin's Lymphomas."

Foran J.M. et al., *Br. J. Haematol*. 102(1): 149, 1998, "Immunotherapy of mantle cell lymphoma (MCL), lymphoplasmacytoid lymphoma (LPC) and Waldentrom's macroglobulinemia (WM), and small lymphocytic leukemia (SLL) with rituximab (IDEC-C2B8): preliminary results of an ongoing international multicentre trial."

Foran J.M. et al., *J. Clin. Oncol*. 18: 317-24, 2000, "European phase II study of rituximab (chimeric anti-CD20 monoclonal antibody) for patients with newly diagnosed mantle-cell lymphoma and previously treated mantle-cell lymphoma, immunocytoma, and small B-cell lymphocytic lymphoma."

Foran J.M. et al, *British Journal of Haematology*, vol. 102, No. 1, Jul. 1998, p. 243 (1998), "Immunotherapy of Recurrent Follicular Lymphoma (FI) with Rituximab (IDEC-C2B8): Preliminary Results of an Ongoing UK Multicentre Trial".

Ford B. The Cal-Gab: Quarterly Newsletter of the Cancer and Leukemia Group B 7(1): 4-5, Spring 1998. RituxanT (Rituximab).

Ford S.M. et al., *Highlights in Oncology Practice* 16(2): 40-50, 1998, "Immunotherapeutic approaches to treatment of B-cell neoplasms: focus on unconjugated antibodies."

Freedman A.S. et al., *J. Clin. Oncol*. 8: 784-91, 1990, "Autologous bone marrow transplantation in B-cell non-Hodgkin's lymphoma: very low treatment-related mortality in 100 patients in sensitive relapse."

Fridik M.A. et al., *Ann. Hematol*. 74(1): 7-10, 1997, "First-line treatment of Waldenstrom's disease with cladribine."

Friedberg J.W. et al., *Expert Rev. Anticancer Ther*. 4(1): 18-26, 2004, "Iodine-131 tositumomab (Bexxar®): radioimmunoconjugate therapy for indolent and transformed B-cell non-Hodgkin's lymphoma."

Garcia-Conde J. et al., *Blood*, vol. 94, No. 10 Suppl. 1 Part 2, p. 261b Nov. 15, 1999, "Study to Evaluate the Efficacy and Safety of Rituximab (IDEC-C2B8) and CVP Chemotherapy in Low-Grade or Follicular B-Cell Lymphoma After Relapse. Preliminary Results at a Follow Up Period of 3 Months".

Gianni A.M. et al., *Blood* 102: 749-55, 2003, "Long-term remission in mantle cell lymphoma following high-dose sequential chemotherapy and in vivo rituximab-purged stem cell autografting (R-HDS regimen)".

Ginaldi L. et al., *J. Clin. Pathol*. 51: 364-69, 1998, "Levels of expression of CD19 and CD20 in chronic B leukaemias."

Gladstone et al, *Leuk Lymphoma*. Nov. 2011; 52 (11): pp. 2076-2081, "High-dose cyclophosphamide and rituximab without stem cell transplant: a feasibility study for low grade B-cell, transformed and mantle cell lymphomas."

Golay J. et al., *Haematologica* 88: 1002-12, 2003, "Rituximab-mediated antibody-dependent cellular cytotoxicity against neoplastic B cells is stimulated strongly by interleukin-2."

Golay J.T. et al., *J. Immunol*. 135(6): 3795-801, 1985, "The CD20 (Bp35) antigen is involved in activation of B cells from the G0 to the G1 phase of the cell cycle."

Goldenberg D.M. et al., *J. Clin. Oncol*. 9(4): 548-64, 1991, "Imaging and therapy of gastrointestinal cancers with radiolabeled antibodies."

Goldenberg, et al., *Poster Session: Biologic Therapy of Lymphomas: Laboratory Investigations*, 2004, "Characterization of New, Chimeric and Humanized, Anti-CD20 Monoclonal Antibodies, cA20 and hA20, with Equivalent Efficacy to Rituximab In-Vitro and in Xenografted Human Non-Hodgkin's Lymphoma", 1 pg.

Gonzalez-Barca et al., *Eur. J. Hemat*. 62(4): 231-238 (1999), "Low-dose subcutaneous interleukin-2 in patients with minimal residual lymphoid neoplasm disease,".

A. Gopal et al., *J. Lab Clin Med*; 134:, 1999, "Clinical applications of anti-CD20 antibodies", pp. 445-450.

Gordon L.I. et al. *Blood* 94(10 Suppl. 1): 91a, abst. No. 396, 1999. "Zevalin™ (IDEC-Y2B8) radioimmunotherapy of rituximab refractory follicular non-Hodgkin's lymphoma (NHL): interim results."

Gordon L.I. et al. *J. Immunother*. 22(5): 459, 1999. "Update on IDEC-Y2B8 (Zevalin™) radioimmunotherapy of B-cell NHL."

Greenberger J.S. et al. *Cancer Res*. 45(2): 758-67, 1985. "Effects of monoclonal antibody and complement treatment of human marrow on hematopoiesis in continuous bone marrow culture."

Greiner J.W. et al. *Science* 235(4791): 895-98, 1987. "Recombinant interferon enhances monoclonal antibody-targeting of carcinoma lesions in vivo."

Gribben J.G. et al. *N. Engl. J. Med*. 325(22): 1525-32, 1991. "Immunologic purging of marrow assessed by PCR before autologous bone marrow transplantation for B-cell lymphoma."

Grillo-Lopez A.J. IBC Int'l. Conference on Antibody Engineering, La Jolla, Dec. 1994. "IDEC-C2B8 chimeric antibody and IDEC-Y2B8 radiolabeled antibody phase I and II studies in patients with non-Hodgkin's lymphoma (abstract of presentation)."

Grillo-Lopez A.J. et al. *Ann. Oncol*. 7(3 Suppl.): 57, abst. No. 195, 1996. "Treatment (rx) of relapsed non-Hodgkin's lymphoma (NHL) using the 90-yttrium (90-Y) labeled anti-CD20 monoclonal antibody (MAB) IDEC-Y2B8: a phase J. Clinical trial (PI CT)."

Grillo-Lopez A.J. et al. *Antibody Immunoconj. Radiopharm*. 8: 60, abst. No. 10, 1995. "Treatment options for patients with relapsed low-grade or follicular lymphoma: the role of IDEC-C2B8."

Grillo-Lopez A.J. et al. *Blood* 86(10 Suppl. 1): 55a, abst. No. 207, 1995. "Phase 1 study of IDEC-Y2B8: 90-yttrium labeled anti-CD20 monoclonal antibody therapy of relapsed non-Hodgkin's lymphoma."

Grillo-Lopez A.J. et al. *Br. J. Haematol*. 93(Suppl. 2): 283, abst. No. 1072, 1996. "IDEC-C2B8 chimeric anti-CD20 antibody (MAB): safety and clinical activity in the treatment of patients (PTS) with relapsed low-grade or follicular (IWF:A-D) non-Hodgkin's lymphoma (NHL)."

Grillo-Lopez, *Seminars in Oncology*, vol. 27, No. 6, Suppl 12 (Dec. 2000); pp. 9-16, "Rituximab: An Insider's Historical Perspective".

Grillo-Lopez et al., *Seminars in Oncology*, vol. 26, No. 5, Suppl 14 (Oct. 1999); pp. 66-73, "Overview of the Clinical Development of Rituximab: First Monoclonal Antibody Approved for the Treatment of Lymphoma".

Grillo-Lopez et al., "Monoclonal Anti-CD20 Antibody (IDEC-C2B8) Therapy of B-Cell Non-Hodgkin's Lymphoma—Pre Clinical Development and Early Clinical Results", *Proc Eighth NCI/EORTC Symposium on New Drugs in Cancer Therapy*, p. 112 (#175) Mar. 1994.

Grillo-Lopez et al., *Exp Hematol* Abstract 17, vol. 25, No. 8, p. 732, Aug. 1997."Development of Response Criteria (RC) for Low-Grade or Follicular Lymphomas (LG/F NHL) and Application in a 166 Patient Study", 26th Annual Meeting of the International Society for Experimental Hematology.

Grillo-Lopez, *Ann Hematol* 77(Suppl 1):A7 (#26), 1998. "Rituximab (IDEC-C2B8): Development of an anti-CD20 monoclonal antibody (MAB) for the treatment of non-Hodgkin's lymphoma."

Grillo-Lopez et al., *Antibody Immunoconjugates, and Radiopharmaceuticals*, vol. 7, No. 1, Abstract 64, Spring 1994, p. 91, "Preclinical and Early Clinical Development of the Anti-CD20

(56) References Cited

OTHER PUBLICATIONS

Monoclonal Antibody IDEC-C2B8", Ninth International Conference on Monoclonal Antibody Immunoconjugates for Cancer.
Grillo-Lopez et al., Ann Oncol 7(1 Suppl):56, Mar. 1996, "IDEC-C2B8: Clinical development of a chimeric anti-CD20 antibody for the treatment of patients (pts) with relapsed low-grade or follicular NHL", Abstract 190.
Grillo-Lopez et al., Exp Hematol 26(8):746 (#233), Aug. 1998, "Rituxan™: Anti CD20 monoclonal antibody for the treatment of lymphoma."
Grillo-Lopez et al., J. Mol. Med. Abstract 259, vol. 75, No. 7, Jul. 1997, pp. B231-B232, "Overview of the safety and efficacy of IDEC-C2B8 including activity in patient populations with poor prognosis low grade or follicular NHL (LG/F NHL)".
Grillo-Lopez et al., Exp Hematol Abstract 406, vol. 25, No. 8, Aug. 1997, pp. 846 "IDEC-C2B8 (Rituximab): Clinical Activity in Poor Prognosis Subgroups of Relapsed Low-Grade or Follicular Lymphoma", 26th Annual Meeting of the International Society for Experimental Hematology.
Grillo-Lopez A.J. IBC Int'l. Conference on Antibody Engineering, La Jolla, Dec. 1994. "IDEC-C2B8 chimeric antibody and IDEC-Y2B8 radiolabeled antibody phase I and II studies in patients with non-Hodgkin's lymphoma (abstract of presentation)."
Grillo-Lopez et al., Exp Hematol Abstract 691, vol. 24, No. 9, Aug. 1996, pp. 1150, "Anti-CD20 Chimeric Antibody, IDEC-C2B8: Safety and Clinical Activity in the Treatment of Relapsed Low Grade or Follicular (IWF: A-D) Lymphomas (LG-F/NHL)", 25th Annual Meeting of the International Society for Experimental Hematology.
Grillo-Lopez et al., Eur J Cancer 33 (S8):S260-S261 (#1179), Sep. 1997. "Clinical activity of the monoclonal antibody (MAB) IDEC-C2B8 in patients (pts) with relapsed low-grade or follicular NHL (R-LG/F NHL)".
Grillo-Lopez et al., Blood 92(10 Suppl 1):412a (#1701), Nov. 1998. "Response criteria (RC) for NHL: Importance of "normal" lymph node (LN) size and correlations with response."
Grillo-Lopez, Journal of Immunotherapy with Emphasis on Tumor Immunology, vol. 16, No. 3, Oct. 1994, pp. 236 "IDEC-C2B8: Initial Phase II Results in Patients with B-Cell Lymphoma".
Grossbard M.L. et al. Blood 80(4): 863-78, 1992. "Monoclonal antibody-based therapies of leukemia and lymphoma."
Grossbard M.L. and Multani, P.S., "Clinical Status and Optimal Use of Rituximab for B-Cell Lymphomas", Oncology vol. 12(12); 1998, pp. 1-2, as published online by www.cancernetwork.com.
Grossbard M.L. "The McLaughlin et al Article Reviewed", Dec. 1998, Oncology, pp. 1769-1770.
Guan, et al., Chinese Journal of Clinical Oncology, vol. 4, No. 4, pp. 264-267, (207) "Rituximab in combination with CHOP, an effective and well-tolerated salvage regimen for diffuse large B-Cell Lymphoma".
Gura T. Science 278: 1041-42, 1997. "Systems for identifying new drugs are often faulty."
Habermann, et al., J Clin Oncol 24 (19): 3121-7, 2006. "Rituximab-CHOP versus CHOP alone or with maintenance rituximab in older patients with diffuse large B-cell lymphoma", [PUBMED Abstract].
Habermann, et al., Blood 104 (11): A-127, 2004. "Rituximab-CHOP versus CHOP with or without maintenance rituximab in patients 60 years of age or older with diffuse large B-cell lymphoma (DLBCL): an update" [Abstract].
Hagenbeek A. et al. J. Clin. Oncol. 16(1): 41-47, 1998. "Maintenance of remission with human recombinant interferon alfa-2a in patients with stages III and IV low-grade malignant non-Hodgkin's lymphoma." European Organization for Research and Treatment of Cancer Lymphoma Cooperative Group.
Hainsworth J.D. et al. Blood 95: 3052-56, 2000. "Rituximab monoclonal antibody as initial systemic therapy for patients with low-grade non-Hodgkin lymphoma."
Hainsworth et al., "Rituximab Induction and Maintenance Therapy in Patients (pts) with Previously Untreated Low-Grade Non-Hodgkin's Lymphoma (NHL): Preliminary Results of a Minnie Pearl Cancer Research Network Phase II Trial" Proceedings of the ASCO, vol. 18 (Abstract #105) 1999, p. 29a ; with e-mail from Ascopubs [ascobus@asco.org] dated Mar. 11, 2013, 1 pg, stating that the 1999 Program Proceedings vol. 18 was made available to the public on May 15, 1999.
Hancock et al., Cancer Res. 51(17): 4575-80 (1991), "A monoclonal antibody against the c-erbB-2 protein enhances the cytotoxicity of cis-diamminedichloroplatinum against human breast and ovarian tumor cell lines".
Harris N.L. et al. Blood 84(5): 1361-92, 1994. A revised European-American classification of lymphoid neoplasms: a proposal from the International Lymphoma Study Group.
Harris N.L. et al. J. Clin. Oncol. 17(12): 3835-49, 1999. World Health Organization classification of neoplastic diseases of the hematopoietic and lymphoid tissues: report of the Clinical Advisory Committee meeting—Airlie House, Virginia, Nov. 1997.
Hartwell L.H. et al. Science 278: 1064-68, 1997. "Integrating genetic approaches into the discovery of anticancer drugs."
Hekman A. et al. Ann. Rept. Netherlands Cancer Inst., Amsterdam, pp. 47-48, 1993. "Immunotherapy."
Herold M. et al. Ann. Hematol. 79: 332-335, 2000. "Successful treatment and re-treatment of resistant B-cell chronic lymphocytic leukemia with the monoclonal anti-CD20 antibody rituximab."
Hiddemann W. et al. Blood 88(11): 4085-89, 1996. "Lymphoma classification—the gap between biology and clinical management is closing."
Hiddemann, European Journal of Cancer vol. 31A (13/14) 1995, pp. 2141-2145, "Non-Hodgkin's Lymphomas—Current Status of Therapy and Future Perspectives".
Hiddemann, et al. Lymphome, Neue Erkenntnisse and Therapiestrategien, Klinische Symptomatik, pp. 78-81 (2005) Translated.
Hillmen P. et al. Semin. Oncol. 31(1 suppl. 2): 22-26, 2004. "Advancing therapy for chronic lymphocytic leukemia—the role of rituximab."
Hochster, H.S., et al., Journal of Clinical Oncology, 2004 ASCO Annual Meeting, vol. 22, No. 14S (Jul. 15 Supplemental), 2004: 6502, "Results of E1496: A phase III trial of CVP with or without maintenance rituximab in advanced indolent lymphoma (NHL)", pp. 1-2.
Hochster H., et al.: "Maintenance Rituximab After CVP Results in Superior Clinical Outcome in Advanced Follicular Lymphoma (FL) : Results of the E1496 Phase III Trial From the Eastern Cooperative Oncology Group and the Cancer and Leukemia Group B" Blood (ASH Annual Meeting Abstracts), 2005, 106: Abstract 349, vol. 106, No. 11, pt. 1, Nov. 1, 2005 (Nov. 1, 2005), p. 106A.
Hochster et al., J. Clin. Oncol. 27(10): 1607-1614 (2009), "Maintenance rituximab after cyclophosphamide, vincristine, and prednisone prolongs progression-free survival in advanced indolent lymphoma: Results of the randomized phase III ECOG1496 Study".
Hooijberg E. et al. Cancer Res. 55: 2627-34, 1995. "Eradication of large human B cell tumors in nude mice with unconjugated CD20 monoclonal antibodies and interleukin 2."
Horning S.J. et al. Blood 100(11 part 1): 357a, abst. No. 1385, 2002. "Rituximab treatment failures: tositumomab and Iodine I 131 tositumomab (Bexxar®) can produce meaningful durable responses."
Horning et al., Proc Am Soc Clin Oncol 16:18a (#62), May 1997, "Response criteria (RC) and quality assurance (QA) of responses in the evaluation of new therapies for patients (pts) with low-grade lymphoma (LG NHL)".
Hurwitz E. et al., Intl. J. Cancer 37(5): 739-45 (May 1986). "A Synergistic Effect Between Anti-Idiotype Antibodies and Antineoplastic Drugs in the Therapy of a Murine B-Cell Tumor."
Hultin et al., Cytometry 14(2), 1993, pp. 196-204, "CD20 (pan-B cell) antigen is expressed at a low level on a subpopulation of human T lymphocytes", (Abstract only), www.ncbi.nlm.nih.gov/pubmed/7679964.
IDEC Pharmaceuticals "IDEC Pharmaceuticals Announces Positive Preliminary Results for Pivotal Trial of IDEC-C2B8" press release, May 21, 1996 (USA).

(56) References Cited

OTHER PUBLICATIONS

IDEC Pharmaceuticals Corp. and Genentech, Inc., Product insert for Rituxan® approved by U.S. Food and Drug Administration on Nov. 26, 1997.
IDEC Pharmaceuticals Corp., press release dated Dec. 9, 1996. IDEC Pharmaceuticals and Genentech announce positive final results for pivotal phase III trial of IDEC-C2B8 as single agent.
IDEC Pharmaceuticals Corp., U.S. Securities and Exchange Commission Form S-1 Registration Statement, 1991.
*IDEC Pharmaceuticals v. Corixa Corp.*, Case No. 01-1637-IEG [Doc. Nos. 486, 584] (S.D. Cal.) Oct. 14, 2003.
Imrie K. et al., *Curr. Oncol.* 6(4): 228-35, 1999. "Use of rituximab in the treatment of lymphoma: an evidence summary."
Jain R.K., *Sci. Am.* 271(1): 58-65, 1994. "Barriers to drug delivery in solid tumors."
James, J.S. and Dubs, G., *AIDS Treat News* (No. 284): 2-3, 1997, "FDA approves new kind of lymphoma treatment. Food and Drug Administration" 1 pg. (Abstract only).
Janakiraman N. et al., *Blood* 92(10 Suppl. 1): 337a, abst. No. 1384, Nov. 1998. "Rituximab: correlation between effector cells and clinical activity in NHL."
Jazirehi A.R. et al., *Oncogene* 24: 2121-43, 2005. "Cellular and molecular signal transduction pathways modulated by rituximab (rituxan, anti-CD20 mAb) in non-Hodgkin's lymphoma: implications in chemosensitization and therapeutic intervention."
Jensen M. et al., *Ann. Hematol.* 77: 89-91, 1998. "Rapid tumor lysis in a patient with B-cell chronic lymphocytic leukemia and lymphocytosis treated with an anti-CD20 monoclonal antibody (IDEC-C2B8, rituximab)."
Juweid M. et al., *Cancer Res.* 55(23 Suppl.): 5827s-5831s, 1995. "Estimates of red marrow dose by sacral scintigraphy in radioimmunotherapy patients having non-Hodgkin's lymphoma and diffuse bone marrow uptake."
Juweid M. et al., *Cancer Res.* 55(23 Suppl.): 5899s-5907s, 1995. "Treatment of non-Hodgkin's lymphoma with radiolabeled murine, chimeric, or humanized LL2, an anti-CD22 monoclonal antibody".
Kaminski M. et al., *Antibody Immunoconj. Radiopharm.* 3(1): abst. No. 83, 1990. "Radioimmunotherapy of advanced B-cell lymphoma with non bone marrow ablative doses of 131-I MB-1 antibody."
Kaminski M. et al., *Antibody Immunoconj. Radiopharm.* 4(1): 36, abst. No. 66, 1991. "Phase I trial results of 131-1 antibody radioimmunotherapy (RAIT) of B-cell lymphoma."
Kaminski M. et al., *J. Clin. Oncol.* 10(11): 1696-1711, 1992. "Imaging, dosimetry, and radioimmunotherapy with iodine 131-labeled anti-CD37 antibody in B-cell lymphoma."
Kaminski M. et al., *Proc. Amer. Soc. Clin. Oncol.* 9: 271, abst. No. 1051, 1990 "Radioimmunodetection (RID) and non marrow ablative radioimmunotherapy (RIT) of B-cell lymphoma with 131-I MB-1 antibody."
Kaminski M. et al. Proc. Third Conf. on Radioimmunodetection and Radioimmunotherapy of Cancer, Princeton NJ, Nov. 15-17, 1990 (published at Antibody Immunoconj. Radiopharm. 4: 387, 1991), abst. No. 144. "131-1 anti-B1: Initial clinical evaluation in B-cell lymphoma."
Kaminski M. et al., *Antibody Immunoconj. Radiopharm.* 5(3): 345, abst. No. 57, 1992. "Initial clinical radioimmunotherapy results with $^{131}$I-anti-B1 (anti-CD20) in refractory B-cell lymphoma."
Kaminski M. et al., *Blood* 76(10 Suppl. 1): 355a, abst. No. 1409, 1990. "Phase I evaluation of 131-1 MB-1 antibody radioimmunotherapy (RIT) of B-cell lymphoma."
Kaminski M. et al., *Blood* 78(10 Suppl. 1): 43a, abst. No. 161, 1992. "Radioimmunotherapy (RIT) of refractory B-cell lymphoma with 131-I-anti-B1 (anti-CD20) antibody: promising early results using non-marrow ablative radiation doses."
Kaminski M. et al., *J Clin. Oncol.* 14(7): 1974-81, 1996. "Iodine-131-anti-B1 radioimmunotherapy for B-cell lymphoma."
Kaminski M. et al., *N. Engl. J Med.* 329: 459-65, 1993. "Radioimmunotherapy of B-cell lymphoma with [$^{131}$I]anti-B1 (anti-CD20) antibody."

Keating M. et al., *Semin. Oncol.* 27(6 suppl. 12): 86-90, 2000. "High-dose rituximab therapy in chronic lymphocytic leukemia."
Kennedy et al., *Br. J. Haematol.* 119(2) 412-6 (2002), "Incidence and nature of CD20-negative relapses following rituximab therapy in aggressive B-cell non-Hodgkin's lymphoma: a retrospective review".
Khan et al., *Clin Cancer Res* 12(23):7046-7053 (2006), "A Phase 2 Study of Rituximab in Combination with Recombinant Tnterleukin-2 for Rituximab-Refractory Indolent Non-Hodgkin's Lymphoma,".
Kimby, *Semin. Oncol.* 29(2 Suppl. 6): 7-10 (2002) "Beyond immunochemotherapy: combinations of rituximab with cytokines interferon-alpha2a and granulocyte colony stimulating factor".
Kimura et al., "VII Medicaments for hematologic diseases 'lymphoid malignancy'; 177. Drug therapies for non-Hodgkin's lymphoma" *Medicina* vol. 24, No. 10 (1987), pp. 2194-2197 (English translation of Japanese Office Action dated Dec. 25, 2012, filed in corresponding JP Patent Application No. 2000-564662 attached).
King and Younes, *Expert Rev. Anticancer Ther.* 1(2): 177-86 (2001) "Rituximab: review and clinical applications focusing on non-Hodgkin's lymphoma,"
Kinoshita T. et al., *J. Clin. Oncol.* 16(12): 3916, Dec. 1998. "CD20-negative relapse in B-cell lymphoma after treatment with Rituximab."
Klarnet J.P. et al., *J. Immunol.* 138(11): 4012-17, 1987. "Antigen-driven T cell clones can proliferate in vivo, eradicate disseminated leukemia, and provide specific immunologic memory."
Knox S.J. et al., Clin. *Cancer Res.* 2: 457-70, 1996. "Yttrium-90-labeled anti-CD20 monoclonal antibody therapy of recurrent B-cell lymphoma."
Knox S.J. et al., *I. J. Rad. Oncol. Biol. Phys.* 32: 215, 1995. "$^{90}$Y-anti-CD20 monoclonal antibody therapy for recurrent B cell lymphoma."
Knox S.J. et al., *J. Immunother.* 16(2): 161, abst. No. 51, 1994. "$^{90}$Y-anti-CD20 monoclonal antibody therapy (IDEC-Y2B8) for recurrent B cell lymphoma."
Kuzel T. et al., *Cancer Biother.* 8(1): 3-16, 1993. "A phase I escalating-dose safety, dosimetry and efficacy study of radiolabeled monoclonal antibody LYM-1."
Langmuir V.K., *Nucl. Med. Biol.* 19(2): 213-55, 1992. "Radioimmunotherapy: clinical results and dosimetric considerations."
Larson S.M. et al., *Nucl. Med. Biol.* 16: 153-58, 1989. "Comparison of bone marrow dosimetry and toxic effect of high dose $^{131}$I-labeled monoclonal antibodies administered to man."
Lauria F. et al., *Bone Marrow Transplant.* 18(1): 79-85, 1996. "Immunologic and clinical modifications following low-dose subcutaneous administration of rIL-2 in non-Hodgkin's lymphoma patients after autologous bone marrow transplantation."
Lazzarino et al., *Oncology.* 2005;68(2-3): pp. 146-153 "Immunochemotherapy with rituximab, vincristine and 5-day cyclophosphamide for heavily pretreated follicular lymphoma."
Lefrak et al., *Cancer* 32(2) 1973, pp. 302-314, "A clinicopathologic analysis of adriamycin cardiotoxicity" (Abstract only).
Leget et al., *Current Opinion in Oncology* 10, 1998, pp. 548-551, "Use of rituximab, the new FDA-approved antibody".
Leichner P.K. et al. *Front. Rad. Ther. Oncol.* 24: 109-20, 1990. "Dosimetry and treatment planning in radioimmunotherapy."
Leichner P.K. et al. *Med. Phys.* 20(2): 529-34, 1993. "Tumor dosimetry in radioimmunotherapy: methods of calculation for beta particles."
Levy R. et al. *Fed. Proc.* 42: 2650-56, 1983. "Tumor therapy with monoclonal antibodies."
Ling N.R. et al. (in) Leucocyte Typing III: White Cell Differentiation Antigens, A.J. McMichael et al., eds., Oxford: Oxford Univ. Pr., 1987, pp. 302-335. "B-cell and plasma cell antigens: new and previously defined clusters."
Link B.K. et al. *Proc. Amer. Soc. Clin. Oncol.* 17: 3a, abst. No. 7, 1998. "Phase II pilot study of the safety and efficacy of rituximab in combination with CHOP chemotherapy in patients with previously untreated intermediate- or high-grade NHL."
Link M.P. et al. *J. Immunol.* 137(9): 3013-18, 1986. "A unique antigen on mature B-cells defined by a monoclonal antibody."

(56) References Cited

OTHER PUBLICATIONS

Lipton J.M. et al.*Blood* 60(5 Suppl. 1): 170a, abst. No. 609, 1992. "Distribution of B1, CALLA, β2 microglobulin and Ia on hematopoiesis supporting cells (HSC) in short and long-term cultures."

Lister, "The management of follicular lymphoma", *Annals of Oncology*, Supplement 2, vol. 2, pp. 131-135, (1991).

Liu A.Y. et al. *J. Immunol.* 139(10): 3521-26, Nov. 1987. "Production of a mouse-human chimeric monoclonal antibody to CD20 with potent Fc-dependent biologic activity."

Lonberg N. et al. *Nature* 368: 856-59, 1994. "Antigen-specific human antibodies from mice comprising four distinct genetic modifications".

Longo D.L., *Curr. Opin. Oncol.* 8(5): 353-59 (Sep. 1996) "Immunotherapy for Non-Hodgkin's Lymphoma."

Lowman H.B. Slides presented at IBC Antibody Engineering Conference, Dec. 2, 2003. "Differential activities in a series of humanized anti-CD20 antibodies."

Lum L.G. et al. *Blood* 69(2): 369-80, 1987. "The kinetics of immune reconstitution after human marrow transplantation."

Macey D.J. et al. *Front. Rad. Ther. Oncol.* 24: 123-31, 1990. "A treatment planning program for radioimmunotherapy".

Macklis R.M. et al. *Antibody Immunoconj. Radiother.* 5(3): abst. No. 39, 1992. "Induction of programmed cell death in malignant lymphomas after radioimmunotherapy."

Macklis R.M. et al. *Cancer* 73(3 Suppl.): 966-73, 1994. "Radiobiologic studies of low-dose-rate $^{90}$Y-lymphoma therapy."

Maddy A.H. et al. *Immunol.* 68(3): 346-52, 1989. "The role of cell maturation in the generation of phenotypic heterogeneity in B-cell chronic lymphocytic leukaemia."

Maloney D.G. et al. *Blood* 90(6): 2188-2195, 1997. "IDEC-C2B8 (Rituximab) anti-CD20 monoclonal antibody therapy in patients with relapsed low-grade non-Hodgkin's lymphoma."

Maloney D.G. et al. *Blood* 80(6): 1502-1510, 1992. "Monoclonal anti-idiotype antibody therapy of B-cell lymphoma: the addition of a short course of chemotherapy does not interfere with the antitumor effect nor prevent the emergence of idiotype-negative variant cells."

Maloney D.G. et al. *Blood* 84(8): 2457-66, 1994. "Phase 1 clinical trial using escalating single-dose infusion of chimeric anti-CD20 monoclonal antibody (IDEC-C2B8) in patients with recurrent B-cell lymphoma."

Maloney D.G. et al. *Blood* 88(10: Suppl. 1): 637a, abst. No. 2635, 1996. "The anti-tumor effect of monoclonal anti-CD20 antibody (mAb) therapy includes direct anti-proliferative activity and induction of apoptosis in CD20 positive non-Hodgkin's lymphoma (NHL) cell lines."

Maloney D.G. et al. *J. Clin. Oncol.* 15(10): 3266-74, "IDEC-C2B8: results of a phase 1 multiple-dose trial in patients with relapsed non-Hodgkin's Lymphoma." Oct. 1997.

Maloney et al., *Journal of Clinical Oncology*, vol. 15, No. 10, Oct. 1977, pp. 3266-3274, "IDEC-C2B8: Results of a Phase I Multiple-Dose Trial in Patients with Relapsed Non-Hodgkin's Lymphoma".

Maloney, D.G., et al., *Proc Am Soc Clin Oncol* 13:304 (#993) Mar. 1994, "Initial Report on a Phase VII Multiple Dose Clinical Trial of IDEC-C2B8 (Chimeric Anti-CD20) in Relapsed B-Cell Lymphoma".

Maloney et al., *Cancer Investigation*, vol. 13, Suppl 1, pp. 31-32 (#24), 1995, "Phase I/II Clinical Trials of IDEC-C2B8 (Chimeric Anti-CD20 Antibody) in Relapsed B-Cell Lymphoma".

Maloney, D.G., et al., *Cancer Investigation* 15(1 Suppl):78-79 (#70), 1997, "Chimeric Anti-CD20 (IDEC-C2B8) Monoclonal Antibody Therapy of Low-Grade Lymphoma".

Maloney, D.G., et al., *Blood* 86(10):54a (#205), Nov. 1995. "IDEC-C2B8 Anti-CD20 Antibody: Results of Long-Term Follow-Up of Relapsed NHL Phase II Trial Patients".

Maloney, D.G., et al., *Blood* 84(10) Supplement 1:169a (#661), 1994. "IDEC-C2B8: Final report on a Phase II trial in relapsed non-Hodgkin's lymphoma".

Maloney, D.G., et al., *Blood* 82(10 Suppl 1): 445a (#1763), Nov. 1993 "Phase I Clinical Trial Using Escalating Single Dose Infusion of Chimeric Anti-CD20 Monoclonal Antibody (IDEC-C2B8) in Patients with Recurrent B-Cell Lymphoma)".

Mangel et al., *Semin. Oncol.* 29(1 Suppl. 2): 56-69 (2002), "Immunotherapy with rituximab following high-dose therapy and autologous stem-cell transplantation for mantle cell lymphoma,".

Maloney et al., "Newer Treatments for Non-Hodgkin's Lymphoma: Monoclonal Antibodies", Oncology vol. 12, No. 10, Oct. 2, 1998, pp. 1-21 http://www.cancernetwork.com/display/article/10165/72098 (Retrieved 1998).

Marcus et al., *Blood* 105: 1417-1423 (2005) "CVP chemotherapy plus rituximab compared with CVP as first-line treatment for advanced follicular lymphoma,".

Mariuzza et al. *Science*. 233: 747-53, 1986. "Three-dimensional structure of an antigen-antibody complex at 2.8 Å resolution."

Marquez S.D. et al. *I.J. Rad. Oncol. Biol. Phys.* 39: 327, abst. No. 2173, 1997. "Hematological toxicity in radioimmunotherapy is predicted both by the computed absorbed whole body dose (cGy) and by the administered dose (mCi)."

Marti G.E. et al. *Ann. N.Y. Acad. Sci.* 651: 480-83, 1992. "CD20 and CD5 expression in B-chronic lymphocytic leukemia."

Marx J.L. *Science* 229(4712): 455-56, 1985. "Antibodies made to order."

Masucci G. et al. *Med. Oncol. Tumor Pharmacother.* 8(3): 207-20, 1991. "Chemotherapy and immunotherapy of colorectal cancer."

Mazza P. et al. *Bone Marrow Trans.* 23: 1273-78, 1999. "Analysis of feasibility of myeloablative therapy and autologous peripheral stem cell (PBSC) transplantation in the elderly: an interim report."

McLaughlin P. et al. *Blood* 92(10 Suppl. 1): 414a-415a, abst. No. 1712, Nov. 1998. "Efficacy controls and long-term follow-up for relapsed or refractory, low-grade or follicular (R-LG/F) NHL."

McLaughlin P. et al. *J. Clin. Oncol.* 16(8): 2825-33, Aug. 1998. "Rituximab chimeric-anti-CD20 monoclonal antibody therapy for relapsed indolent lymphoma: half of patients respond to a four-dose treatment program. (Received by Univ. of Minn. Biomedical Library: Aug. 10, 1998.)".

McLaughlin P. et al. *Oncology* 12(12): 1763-81, 1998. "Clinical status and optimal use of rituximab for B-cell lymphomas."

McLaughlin et al., *J. Mol. Med.* 75 (7):B231 (#257), Jul. 1997. "A Phase III (PIII) pivotal trial of IDEC-C2B8 in patients (pts) with relapsed low-grade or follicular lymphoma."

McLaughlin et al., *Semin Oncol* 26(5, 14 Suppl):79-87, Oct. 1999 "Rituximab in Indolent Lymphoma: The Single-Agent Pivotal Trial".

McLaughlin et al., *Proc Am Soc Clin Oncol* 16:16a (#55), May 1997 "IDEC-C2B8 (Rituximab): Clinical activity in clinically-chemoresistant (CCRD) low-grade or follicular lymphoma (LG/F NHL) and in patients (pts) relapsing after anthracycline therapy (ANTHRA-RX) or ABMT."

McLaughlin ct al., *Ann Oncol* 7 (3 Suppl):57 (#194), Jun. 1996. "Pivotal Phase III clinical trial (PIII CT) of the chimeric anti-CD20 antibody (MAB) IDEC-C2B8 in patients (PTS) with relapsed low-grade or follicular lymphoma (LG/F NHL): A preliminary report".

McLaughlin et al., *Blood* 88(10):90a (#349), Nov. 1996, "IDEC-C2B8 anti-CD20 antibody: Final report on a Phase III pivotal trial in patients (PTS) with relapsed low-grade or follicular lymphoma (LG/F NHL)".

McLaughlin et al., *Blood* 88(10 Suppl 1, Part 1 of 2): 90a (#350), (Nov. 1996)."Pharmacokinetics (PK) and Pharmacodynamics (PD) of the anti-CD20 antibody (MAB) IDEC-C2B8 in patients (PTS) with relapsed low-grade or follicular lymphoma (LG/F NHL)".

McLaughlin et al., *Proc Am Soc Clin Oncol* 15:417 (#1281), May 1996. "Preliminary report on a Phase III pivotal trial of the anti-CD20 antibody (MAB) IDEC-C2B8 in patients (PTS) with relapsed low-grade or follicular lymphoma."

Meeker et al., *Blood* 1985; 65: pp. 1349-1363 "A clinical trial of anti-idiotype therapy for B cell malignancy".

Meredith R.F. et al. *J. Nucl. Med.* 33(9): 1648-53, 1992. "Dose fractionation of radiolabeled antibodies in patients with metastatic colon cancer."

Miller et al., *N Engl J Med* 306(9): 517-522, 1982. "Treatment of B-Cell Lymphoma with monoclonal anti-idiotype antibody."

(56) References Cited

OTHER PUBLICATIONS

Mishell B.E. et al., eds. Selected Methods in Cellular Immunology, San Francisco: Freeman, 1980, p. 287-304. "Modification and use of antibodies to label cell surface antigens."

Misset et al., *Annals of Oncology* 10, 1999, pp. 553-560 "Dose-finding study of docetaxel and doxorubicin in first-line treatment of patients with metastatic breast cancer".

Monnereau et al., "L'interféron alpha dans le traitement des lymphomes non hodgkiniens de faible malignité", *Bulletin du Cancer*, vol. 85, No. 10, 1998, pp. 855-865, in French with English translation, pp. 1-19.

Morrison S. et al. *Proc. Nat'l Acad. Sci. USA* 81: 6851-54, 1984, "Chimeric human antibody molecules: mouse antigen-binding domains with human constant region domains".

Morrison S.L. *Science* 229: 1202-07, 1985. "Transfectomas provide novel chimeric antibodies."

Morrison and Peterson, *Leuk. Lymphoma* 10 Suppl.: 29-33 (1993), "Combination chemotherapy in the treatment of follicular low-grade lymphoma".

Morrison, et al., *J Clin Oncol* 25 (Suppl 18): A-8011, 443s, 2007, "Maintenance rituximab (MR) compared to observation (OBS) after R-CHOP or CHOP in older patients (pts) with diffuse large B-cell lymphoma (DLBCL): An Intergroup E4494/C9793 update" [Abstract].

Morrison, et al., *Ann Oncol* 16 (Suppl 5): A-224, v102, 2005, "Dose intensity of Chop alone or with rituximab in diffuse large B-cell lymphoma (DLBCL) in patients >60 years of age: an analysis of the intergroup trial (CALGB 9793, ECOG-SWOG 4494)" [Abstract].

Multani P.S. et al. *J. Clin. Oncol.* 16(11): 3691-3710, 1998. "Monoclonal antibody-based therapies for hematologic malignancies."

Munro A. *Nature* 312: 597, 1984. "Uses of chimeric antibodies."

Murray J.L. et al. *J. Biol. Resp. Modifiers* 9(6): 556-63, 1990. Recombinant alpha-interferon enhances tumor targeting of an antimelanoma monoclonal antibody in vivo.

Murray J.L. et al. *J. Nucl Med.* 26: 3328-29, 1985. "The effect of radionuclide dose on imaging with indium-111-labeled anti P-97 monoclonal antibody."

Muzaffar S. et al. *J. Pak. Med. Assn.* 47(4): 106-09, Apr. 1997 "Immunophenotypic analysis of non-Hodgkin's lymphoma."

Nadler L.M. et al. *Cancer Res.* 40(9): 3147-54, 1980. "Serotherapy of a patient with a monoclonal antibody directed against a human lymphoma-associated antigen."

Nadler L.M. et al. *J. Clin. Invest.* 67: 134-140, 1981. "A unique cell surface antigen identifying lymphoid malignancies of B cell origin."

Nadler L.M. et al. *J. Clin. Invest.* 74(2): 332-40, 1984. "B cell origin of non-T cell acute lymphoblastic leukemia. A model for discrete stages of neoplastic and normal pre-B cell differentiation."

Nadler L.M. et al. *Lancet* 2(8400): 427-31, 1984. "Anti-B1 monoclonal antibody and complement treatment in autologous bone-marrow transplantation for relapsed B-cell non-Hodgkin's lymphoma."

Nakamura K. et al. *Oncology* 50(1): 35-40, 1993. "Effect of alpha-interferon on anti-alpha fetoprotein-monoclonal-antibody targeting of hepatoma."

Neuberger M.S. et al. *Nature* 314: 268-70, 1985. "A hapten-specific chimaeric IgE antibody with human physiological effector function."

Nguyen D.T. et al. *Eur. J. Haematol.* 62: 76-82, 1999. "IDEC-C2B8 anti-CD20 (Rituximab) immunotherapy in patients with low-grade non-Hodgkin's lymphoma and lymphoproliferative disorders: evaluation of response on 48 patients."

Nielsen B. et al. *Eur. J Haematol.* 48(3): 146-51, 1992. "Interferon-a-induced changes in surface antigens in a hairy-cell leukemia (JOK-1), and a Burkitt's lymphoma cell line (Daudi) during in vitro culture."

O'Brien S.*Blood* 92(10 Suppl 1): 105a, abst. No. 431, 1998. "Phase I/II study of rituxan in chronic lymphocytic leukemia (CLL)."

O'Brien S. et al. *N. Engl. J. Med.* 330(5): 319-22, 1994. "Lack of effect of 2-chlorodeoxyadenosine therapy in patients with chronic lymphocytic leukemia refractory to fludarabine therapy."

O'Brien S.M. et al. *J. Clin. Oncol.* 19: 2165-70, 2001. "Rituximab dose-escalation trial in chronic lymphocytic leukemia."

Oettgen H.C. et al. *Hybridoma* 2(1): 17-28, 1983. "Further biochemical studies of the human B-cell differentiation antigens B1 and 132."

Oncology Nursing Society. onsopcontent.ons.org/oes/online_ce/lymph/.05- classification.htm, retrieved Feb. 25, 2003. Current therapies and future directions in the treatment of non-Hodgkin's lymphoma.

Onrust et al., *Drugs* 58(1), 1999, pp. 79-88, "Rituximab".

Orura et al., *Journal of Japan Lymphoreticular System Society*, 1997, 37, 4, 285-296 "Therapeutic future direction with new clinical trials for refractory lymphoid malignancies".

Ozato K. et al. *J. Immunol.* 126(1): 317-21, 1981. Monoclonal antibodies to mouse MHC antigens III. Hybridoma antibodies reacting to antigens of the H-2b haplotype reveal genetic control of isotype expression.

Ozer et al., *Cancer* 82(10): 1821-30 (1998) "Recombinant interferon-alpha therapy in patients with follicular lymphoma".

Palmieri et al., *Oncology Reports* 3: 1996, pp. 733-735 "Maintenance therapy with recombinant interferon alpha-2B (aTFN) in prognostically unfavourable aggressive non-Hodgkin's lymphomas (NHL)".

Panka D.J. et al. *Proc. Nat'l. Acad. Sci.* 85: 3080-84, 1988. "Variable region framework differences result in decreased or increased affinity of variant anti-digoxin antibodies."

Parker B.A. et al. *Cancer Res.* 50(3): 1022s-1028s, 1990. "Radioimmunotherapy of human 13-cell lymphoma with $^{90}$Y-conjugated antiidiotype monoclonal antibody."

Pearson J.W. et al. *Cancer Res.* 49(18): 4990-95, 1989 "Enhanced therapeutic efficacy of an immunotoxin in combination with chemotherapy against an intraperitoneal human tumor xenograft in athymic mice."

Pfreundschuh et al., "CHOP-like chemotherapy plus rituximab versus CHOP-like chemotherapy alone in young patients with good-prognosis diffuse large-B-cell lymphoma: a randomised controlled trial by the MabThera International Trial (MInT) Group", http://oncology.thelancet.com, vol. 7, May 2006, pp. 379-391.

Petryk M. et al. *Oncologist* 6: 317-26, 2001. ASCO 2001: "Critical commentaries: Hematologic malignancies."

Pietersz G.A. et al. *Immunol. Cell. Biol.* 65(2): 111-25, 1987. "The use of monoclonal antibody conjugates for the diagnosis and treatment of cancer."

Piro L. et al. *Blood* 90(10 Suppl. 1): 510a, abst. No. 2272, 1997. "Rituxan™ (rituximab, IDEC-C2B8): Interim analysis of a phase II study of once weekly times 8 dosing in patients with relapsed low-grade or follicular non-Hodgkin's lymphoma."

Piro L.D. et al. *Ann. Oncol.* 10: 655-61, 1999. "Extended Rituximab (anti-CD20 monoclonal antibody) therapy for relapsed or refractory low-grade or follicular non-Hodgkin's lymphoma."

Pitini et al. *Clin Cancer Res* 13(18):5497 (2007) "Interleukin-2 and Lymphokine-Activated Killer Cell Therapy in Patients with Relapsed B-Cell Lymphoma Treated with Rituximab".

Polyak M.J. et al. *Blood* 99: 3256-62, 2002. "Alanine-170 and proline-172 are critical determinants for extracellular CD20 epitopes; heterogeneity in the fine specificity of CD20 monoclonal antibodies is defined by additional requirements imposed by both amino acid sequence and quaternary structure."

Portlock, C.S. and Rosenberg, S.A., *Cancer* 37(3); 1976, pp. 1275-1282 "Combination chemotherapy with cyclophosphamide, vincristine, and prednisone in advanced non-Hodgkin's lymphomas".

Press O. et al. *Proc. Amer. Soc. Clin. Oncol.* 5: 221, abst. No. 864, 1986. "Serotherapy of malignant B cell lymphomas with monoclonal antibody 1F5 (anti-CD20)."

Press O.W. *Cancer Journal* 4(Suppl 2): S19-S26, Jul. 1998. "Prospects for the management of non-Hodgkin's lymphomas with monoclonal antibodies and immunoconjugates."

Press O.W. et al. *Adv. Exp. Med. Biol.* 303: 91-96, 1991. "Radiolabeled antibody therapy of human B cell lymphomas."

Press O.W. et al. *Blood* 69(2): 584-91, 1987. "Monoclonal antibody 1F5 (anti-CD20) serotherapy of human B cell lymphomas."

(56) References Cited

OTHER PUBLICATIONS

Press O.W. et al. *Cancer Res.* 49(17): 4906-12, 1989. "Endocytosis and degradation of monoclonal antibodies targeting human B-cell malignancies."
Press O.W. et al. *J. Clin. Oncol.* 7(8): 1027-38, 1989. "Treatment of refractory non-Hodgkin's lymphoma with radiolabeled MB-1 (anti-CD37) antibody."
Press O.W. et al. *Lancet* 346(8971): 336-40, 1995. "Phase II trial of 131I-B1 (anti-CD20) antibody therapy with autologous stem cell transplantation for relapsed .B cell lymphomas."
Press O.W. et al. *N. Engl. J. Med.* 329(17): 1219-23, 1993. "Radiolabeled-antibody therapy of B-cell lymphoma with autologous bone marrow support."
Press O.W. et al. *Proc. Amer. Soc. Clin. Oncol.* 17, abst. No. 9, May 1998. "A phase I/II trial of high dose iodine-131-anti-B1 (anti-CD20) monoclonal antibody, etoposide, cyclophosphamide, and autologous stem cell transplantation for patients with relapsed B cell lymphomas."
Rai K.R. et al. (in) R. Hoffinan, R., ed., Hematology, 2d. ed., Churchill Livingstone, 1995, Chapter 83, pp. 1308-1319. "Chronic lymphocytic leukemia."
Rapoport et al., *Bone Marrow Transplant.* 29(4): 303-12 (2002) "Autotransplantation for advanced lymphoma and Hodgkin's disease followed by post-transplant rituxari/GM-CSF or radiotherapy and consolidation chemotherapy".
Rastetter et al., *Annu. Rev. Med.*, 55: 477-503 (2004), "Rituximab: expanding role in therapy for lymphomas and autoimmune diseases".
Reff M. et al. *J. Cell. Biochem.* Suppl. 17E: 260, abst. No. T103, 1993. "Depletion of B cells in vivo by a chimeric mouse human monoclonal antibody to CD20."
Reff M.E. et al. *Blood* 83(2): 435-45, 1994. "Depletion of B cells in vivo by a chimeric mouse human monoclonal antibody to CD20."
Reilly R.M., *Clin. Pharm.* 10: 359-75, 1991. "Radioimmunotherapy of malignancies."
Robertson M.J. et al. *Blood* 79(9): 2229-36, 1992. "Human bone marrow depleted of CD33-positive cells mediates delayed but durable reconstitution of hematopoiesis: Clinical trial of MY9 monoclonal antibody-purged autgrafis for the treatment of acute myeloid leukemia."
Robinson R. et al. *Human Antibody Hybrid* 2: 84-93, 1991. "Chimeric mouse-human anti-carcinoma antibodies that mediate different anti-tumor cell biological activities."
Rogers et al., *Ann Oncol* 7(3 Suppl):34 (#108), Jun. 1996 "Clearance of bcl-2 (t14;18) from peripheral blood (PB) and bone marrow (BM) in patients (PTS) with relapsed low-grade or follicular (TWF:A-D) lymphoma (NHL) following single-agent therapy with the chimeric anti-CD20 antibody (MAB) IDEC-C2B8."
Rogers et al., *Proc Annu Meet Am Assoc Cancer Res* 37:213 (#1456), Mar. 1996. "Analysis of bcl-2 t(14;18) translocation in relapsed B-cell lymphoma patients treated with the chimeric anti-CD20 antibody IDEC-C2B8."
Rosenberg et al., *Proc. Amer. Soc. Clin. Oncol* 15:418 (#1282), May 1996 "Pharmacokinetic analysis of serum concentrations of the chimeric anti-CD20 antibody IDEC-C2B8 in patients with relapsed B-cell lymphoma."
Rosenberg *Br. J. Haematol* 93 (2 Suppl):283 (#1071), May 1996. "Pharmacokinetics (PK) of the chimeric anti-CD20 antibody (MAB) IDEC-C2B8: Analysis of serum concentrations in patients (PTS) with relapsed B-cell lymphoma."
Rottenburger C. et al. *Br. J. Haematol.* 106(2): 545-52, 1999. "Clonotypic CD20+ and CD19+ B cells in peripheral blood of patients with multiple myeloma post high-dose therapy and peripheral blood stem cell transplantation."
Rudikoff S. et al. *Proc. Nat'l. Acad. Sci.* 79: 1979-83, 1982. "Single amino acid substitution altering antigen-binding specificity."
Sahagan B.G. et al. *J. Immunol.* 137: 1066-74, 1986. "A genetically engineered murine/human chimeric antibody retains specificity for human tumor-associated antigen."
Saville, Statement of M. Wayne Saville, M.D., dated Dec. 20, 2007, submitted by applicant in Taiwan (R.O.C.) patent application No. 088119557 (Treatment of hematologic malignancies associated with circulating tumor cells using chimeric anti-CD20 antibody, Grillo-Lopez et al., filed Nov. 9, 1999) pp. 1-3.
Scharff M. *Harvey Lectures* 69: 125-42, 1974. "The synthesis, assembly, and secretion of immunoglobulin: a biochemical and genetic approach."
Schlom J. et al. *J. Natl. Cancer Inst.* 82(9): 763-71, 1990. "Advantage of dose fractionation in monoclonal antibody-targeted radioimmunotherapy."
Schulman M. et al. *Nature* 276(5685): 269-70, 1978. "A better cell line for making hybridomas secreting specific antibodies."
Schwartz-Albiez R. et al. *J. Immunol.* 140(3): 905-14, 1988. "The B cell-associated CD37 antigen (gp40-52). Structure and subcellular expression of an extensively glycosylated glycoprotein."
Seaver S. "Monoclonal antibodies in industry: more difficult than originally thought." (1994) *Genetic Engineering News*, 14(14): 19 and 21.
See-Lasley K. et al. *Manual of Oncology Therapeutics*, St. Louis: C.V. Mosby Co., pp. 44-71, 1981. "Hodgkin's disease and non-Hodgkin's lymphoma."
Senter P.D. *FASEB J.* 4: 188-93, 1990. "Activation of prodrugs by antibody-enzyme conjugates: a new approach to cancer therapy."
Senter P.D. et al. *Adv. Exp. Med. Biol.* 303; 97-105, 1991. "Activation of prodrugs by antibody-enzyme conjugates."
Senter P.D. et al. *Cancer Res.* 49: 5789-92, 1989 "Enhancement of the in vitro and in vivo antitumor activities of phosphorylated mitomycin C and etoposide derivatives by monoclonal antibody-alkaline phosphatase conjugates."
Shan D. et al. *Clin. Cancer Res.* 7(8): 2490-95, 2001. "Synergistic effects of the fenretinide (4-HPR) and anti-CD20 monoclonal antibodies on apoptosis induction of malignant human B cells."
Sharkey R.M. et al. *Cancer Res.* 50(3): 964s-969s, 1990. "Biological considerations for radioimmunotherapy."
Shipp et al. *N. Engl. J. Med.* 329(14): 987-94, 1993. The International Non-Hodgkin's Lymphoma Prognostic Factors Project: A predictive model for aggressive non-Hodgkin's lymphoma.
Siddhartha, G. and Vijay, P., *J. Hematology & Oncology* 2:14, pp. 1-7 (Mar. 24, 2009) doi: 10.1186/1756-8722-2-14 "R-CHOP versus R-CVP in the treatment of follicular lymphoma: a meta-analysis and critical appraisal of current literature".
Smalley R.V. et al. *N. Engl. J Med* 327(19): 1336-41, 1992. "Interferon alfa combined with cytotoxic chemotherapy for patients with non-Hodgkin's lymphoma."
Smeland E.B. et al. *J. Immunol.* 138(10): 3179-84, 1987. "Activation of human B cells: alternate options for initial triggering and effects of nonmitogenic concentrations of anti-IgM antibodies on resting and activated cells."
Soiffer R.J. et al. *Blood* 79(2): 517-26, 1992. "Clinical and immunologic effects of prolonged infusion of low-dose recombinant interleukin-2 after autologous and T-cell-depleted allogeneic bone marrow transplantation."
Soiffer R.J. et al. *Blood* 84(3): 964-971, 1994. "Effect of low-dose interleukin-2 on disease relapse after T-cell-depleted allogeneic bone marrow transplantation."
Solal-Celigny P. et al. *J. Clin. Oncol.* 16(7): 2332-38, 1998. "Doxorubicin-containing regimen with or without interferon alfa-2b for advanced follicular lymphomas: final analysis of survival and toxicity in the Groupe d'Etude des Lymphomes Folliculaires 86 Trial."
Srivastava S.C. et al. *Nucl. Med. Biol.* (1.J. Rad. Appl. Tnstrum. B) 18(6): 589-603, 1991. "Progress in research on ligands, nuclides and techniques for labeling monoclonal antibodies."
Stashenko P. et al. *J. Immunol.* 125(4): 1678-85, 1980. "Characterization of Human B Lymphocyte-Specific Antigen."
Staudt L.M. et al. Manuscript from pubmedcentral at NIH, edited paper published at Adv. Immunol 87: 163-208, 2005. "The biology of human lymphoid malignancies revealed by gene expression profiling."
Stenbygaard L.E. et al. *Breast Cancer Res. Treatment* 25: 57-63, 1993. "Toremifene and tamoxifen in advanced breast cancer—a double-blind cross-over trial."

(56) References Cited

OTHER PUBLICATIONS

Steward et al. *Cancer* 61(3) 1988, pp. 441-447 "Maintenance Chlorambucil After CVP in the Management of Advanced Stage, Low-Grade Histologic Type Non-Hodgkin's Lymphoma".
Stewart J.S.W. et al. *Int. J. Cancer Suppl.* 3: 71-76, 1988. "Intraperitoneal $^{131}$I- and $^{90}$Y-labelled monoclonal antibodies for ovarian cancer: pharmacokinetics and normal tissue dosimetry."
Sun L.K. et al. *Hybridoma* 5(Suppl. 1): S17-20, 1986. "Chimeric antibodies with 17-1A-derived variable and human constant regions".
Sweetenham et al., *British Journal of Haematology* 106, 1999, pp. 47-54 "Cost-minimization analysis of CHOP, fludarabine and rituximab for the treatment of relapsed indolent B-cell non-Hodgkin's lymphoma in the U.K."
Tan L.K. et al. *J. Immunol.* 135: 3564-67, 1985. "A human-mouse chimeric immunoglobulin gene with a human variable region is expressed in mouse myeloma cells."
Tedder T.F. et al. *Eur J. Immunol.* 16(8): 881-87, 1986. "Antibodies reactive with the B1 molecule inhibit cell cycle progression but not activation of human B lymphocytes."
Tedder T.F. et al. *J. Immunol.* 135(2): 973-79, 1985. "The B cell surface molecule B1 is functionally linked with B cell activation and differentiation."
Tedder T.F. et al. *J. Immunol.* 141(12): 4388-94, 1988. "Cloning of a complementary DNA encoding a new mouse B lymphocyte differentiation antigen, homologous to the human B1 (CD20) antigen, and localization of the gene to chromosome 19."
Teeling J.L. et al. *Blood* 104: 1793-1800, 2004. "Characterization of new human CD20 monoclonal antibodies with potent cytolytic activity against non-Hodgkin lymphomas."
Teeling J.L. et al. *J Immunol.* 277: 362-71, 2006. "The biological activity of human CD20 monoclonal antibodies is linked to unique epitopes on CD20."
Tobinai K. et al. *Ann. Oncol.* 9(5): 527-34, 1998. "Feasibility and pharmacokinetic study of a chimeric anti-CD20 monoclonal antibody (IDEC-C2B8, rituximab) in relapsed B-cell lymphoma. The IDEC-C2B8 Study Group."
Li Tongdu (chief translator), Clinical Oncology, Anhui Science and Technology Publication, vol. 28-3, pp. 34-45, 1996 and English translation.
Treon et al., *Oncology* 14(3 Suppl. 1): Abstract #521 (2000) "Interferon-Gamma Induces CD20 Expression on Multiple Myeloma Cells via Induction of Pu.1 and Augments Rituximab Binding to Myeloma Cells".
Tsai D.E. et al. *Blood* 92(10 Suppl. 1): 415a, abst. No. 1713, Nov. 1998. "Progressive intermediate grade non-Hodgkin's lymphoma after high dose therapy and autologous peripheral stem cell transplantation (PSCT) has a high response rate to rituximab."
Tsai D.E. et al. *Bone Marrow Transplant.* 24(5): 521-26, 1999. "Rituximab (anti-CD20 monoclonal antibody) therapy for progressive intermediate-grade non-Hodgkin's lymphoma after high-dose therapy and autologous peripheral stem cell transplantation".
Tsai D.E. et al. *Clin. Lymphoma Myeloma* 1(1): 62-66, 2000. "Progressive intermediate-grade non-Hodgkin's lymphoma after high-dose therapy and autologous peripheral stem-cell transplantation: changing the natural history with monoclonal antibody therapy."
Uckun F.M. et al. *Cancer Res.* 45(1): 69-75, 1985. "Increased efficiency in selective elimination of leukemia cells by a combination of a stable derivative of cyclophosphamide and a human B-cell-specific immunotoxin containing pokeweed antiviral protein."
Uckun F.M. et al. *J. Immunol.* 134(5): 3504-15, 1985. "Combined ex vivo treatment with immunotoxins and mafosfamid: a novel immunochemotherapeutic approach for elimination of neoplastic T cells from autologous marrow grafts."
Urlaub G. et al. *Som. Cell. Mot Genet.* 12(6): 555-66, 1986. "Effect of gamma rays at the dihydrofolate reductase locus: deletions and inversions."

Valentine M.A. et al. *J. Biol. Chem.* 264: 11282-87, 1989. "Phosphorylation of the CD20 phosphoprotein in resting B lymphocytes. Regulation by protein kinase C."
van der Kolk L.E. et al., *British Journal of Haematology*, vol. 102, No. 1, Jul. 1998, p. 243, Abstract No. P-0970 "Chimeric Anti-CD20 Monoclonal Antibody (Rituximab) Plus G-CSF in Relapsed B-Cell Lymphoma: A Phase I/II Clinical Trial".
van der Kolk L.E. et al. *Blood* 92(10 Suppl. 1): 241b, abst. No. 4037, Nov. 1998. "Chimeric anti-CD20 monoclonal antibody (rituximab) plus G-CSF in relapsed B-cell lymphoma: a phase I/II clinical trial."
van der Kolk L.E. et al. *Blood* 92(10 Suppl. 1): 512a-513a, abst. No. 2284, 1997. "Phase I/II clinical trial to evaluate the safety and efficacy of a chimeric anti-CD20 monoclonal antibody (rituximab) and G-CSF given weekly to patients with relapsed B-cell lymphoma."
Vartholomatos G. et al. *Acta Haematol.* 102: 94-98, 1999. "Rituximab (anti-CD20 monoclonal antibody) administration in a young patient with resistant B-prolymphocytic leukemia."
Venugopal P. et al. *Blood* 92(10 Suppl. 1): 247a, abst. No. 1009, Nov. 1998. Upregulation of CD20 expression in chronic lymphocytic leukemia (CLL) cells by in vitro exposure to cytokines.
Verkh L.I. et al. *Proc. Amer. Soc. Clin. Oncol.* 17: abst. No. 154, 1998. "Dosimetry results of Oncolym™ in the treatment of refractory B cell non-Hodgkin's lymphoma (NHL)."
Vey N. et al. *Leuk. Lymphoma* 221(1-2): 107-14, 1996. "A pilot study of autologous bone marrow transplantation followed by recombinant interleukin-2 in malignant lymphomas."
Vose J.M. et al. *J. Clin. Oncol.* 19(2): 389-97, 2001. "Phase II study of rituximab in combination with chop chemotherapy in patients with previously untreated, aggressive non-Hodgkin's lymphoma."
Voso et al., *Br. J Haematol* 109(4): 729-35 (2000) "In vivo depletion of B cells using a combination of high-dose cytosine arabinoside/mitoxantrone and rituximab for autografting in patients with non-Hodgkin's lymphoma".
Wadler S. et al. *Semin. Oncol.* 19(2 Suppl. 3): 45-48, 1992. "Principles in the biomodulation of cytotoxic drugs by interferons."
Wahl R.L. et al. *J Nucl. Med.* 31(5): 852, abst. No. 622, 1990. "Radioimmunotherapy of B-cell lymphoma with 1131 MB-1 monoclonal antibody."
Wahl R.L. et al. *Proc. Amer. Soc. Clin. Oncol.* 17: 40a, abst. No. 156, May 1998. "Successful re-treatment of non-Hodgkin's lymphoma (NHL) with iodine-131 anti-B1 antibody."
Weisdorf et al., *J. Clin Oncol* 1992; 10(6): pp. 942-947 "Survival After Relapse of Low-Grade Non-Hodgkin's Lymphoma: Implications for Marrow Transplantation".
Welte K. et al. Blood 64: 380-85, 1984. "Defective interleukin 2 production in patients after bone marrow transplantation and in vitro restoration of defective T lymphocyte proliferation by highly purified interleukin 2."
Wessels B.W. et al. *Med. Phys.* 11(5): 638-45, 1984. "Radionuclide selection and model absorbed dose calculations for radiolabeled tumor associated antibodies."
White C.A. et al. *Ann. Oncol.* 10(3 Suppl): 64, abst. No. 215, 1999. "Radioimmunotherapy of relapsed or refractory non-Hodgkin's lymphoma (NHL): IDEC-Y2B8 phase I/II 90yttrium trial."
White C.A. et al. *Ann. Rev. Med.* 52: 125-45, 2001. "Antibody-targeted immunotherapy for treatment of malignancy."
White C.A. et al. *Blood* 87(9): 3640-49, 1996. "Radioimmunotherapy of relapsed B-cell lymphoma with Yttrium 90 anti-idiotype monoclonal antibodies."
White C.A. et al. *Eur. J. Cancer* 35: S57, abst. No. 107, 1999. "Zevalin™ radioimmunotherapy of relapsed or refractory non-Hodgkin's lymphoma."
White CA et al., *Pharm. Sci. Tech. Today* 2(3): 95-101 "Anti-Cd20 Monoclonal Antibodies as Novel Treatments for Non-Hodgkin's Lymphoma." (Mar. 1999).
White CA, et al., *Eur. J. Cancer* 33(S8): S266, Abstract 1203 "Idec-C2b8-Induced B Cell Depletion is Not Associated With Significant Immune Suppression or Infection." (Sep. 1997).
White et al., *Eur. J. Cancer* 33(5 Suppl):S40 (#91), "Review of single agent IDEC-C2B8 safety and efficacy results in low-grade or follicular non-Hodgkin's lymphoma.", Jun. 1997.

(56) References Cited

OTHER PUBLICATIONS

White et al., *J. Immunother.* 19(6):458, "Anti-CD20 antibody (MAB) IDEC-C2B8 in relapsed low-grade/follicular (LG/F) B-cell non-Hodgkin's lymphoma (NHL). Expanded efficacy and safety results.", Nov. 1996.
White et al., *Proc Annu Meet Am Assoc Cancer Research* 36:638 (#3799) "IDEC-C2B8: Improved tolerance correlated with pharmacodynamic effects in patients with B-cell NHL.", Mar. 1995.
White, *Cancer Biother Radiopharm.* Aug. 1999;14(4): pp. 241-50, "Rituximab immunotherapy for non-Hodgkin's lymphoma."
Winkler U. et al. *Blood* 92(10 Suppl. 1): 285b, abst. No. 4228, Nov. 1998. "Severe side effects in patients with B-cell chronic lymphocytic leukemia (CLL) and lymphocytosis treated with the monoclonal anti-CD20 antibody rituximab."
Winkler U. et al. *Blood* 94: 2217-24, 1999. "Cytokine-release syndrome in patients with B-cell chronic lymphocytic leukemia and high lymphocyte counts after treatment with an anti-CD20 monoclonal antibody (rituximab, IDEC-C2B8)."
Wiseman G. et al. *Blood* 92(10 Suppl. 1): 417a, abst. No. 1721, Nov. 1998. "IDEC-Y2B8 radioimmunotherapy: baseline bone marrow involvement and platelet count are better predictors of hematologic toxicity than dosimetry."
Wiseman G. et al. *Cancer Biother. Radiopharm.* 13(1): 59, abst. No. 22, 1998. "Radioimmunotherapy of relapsed non-Hodgkin's lymphoma (NHL) with IDEC-Y2B8 $^{90}$yttrium anti-CD20 monoclonal antibody."
Wiseman G. et al. *Cancer Biother. Radiopharm.* 13(4): 317, abst. No. 51, 1998. "IDEC-Y2B8 radioimmunotherapy of relapsed non-Hodgkin's lymphoma (NHL): interim analysis."
Wiseman G. et al. *Cancer Biother. Radiopharm.* 14(4): 315, abst. No. 2, 1999. "90Yttrium labelled IDEC Y2B8 anti-CD20 radioimmunotherapy."
Wiseman G. et al. *I. J. Rad. Oncol. Biol. Phys.* 45(10 Suppl): 390, abst. No. 260, 1999. "Radioimmunotherapy of relapsed or refractory non-Hodgkin's Lymphoma (NHL) with IDEC-Y2B8."
Wiseman G. et al. *Proc. Amer. Soc. Clin. Oncol.* 17, 1998. "Radioimmunotherapy of relapsed non-Hodgkin's lymphoma (NHL) with IDEC-Y2B8 $^{90}$yttrium radioimmunotherapy."
Wiseman G.A. et al. *Blood* 92(10 Suppl. 1): 510a, abst. No. 2273, Nov. 1998. "IDEC-Y2B8 ($^{90}$Y conjugated anti-CD20) dosimetry calculated from $^{111}$In anti-CD20 in patients with low and intermediate grade B-cell non-Hodgkin's lymphoma (NHL) emphasis on bone marrow (BM)."
Wiseman G.A. et al. *Blood* 94(10 Suppl. 1): 92a, abst. No. 403, 1999. "Zevalin™ biodistribution and dosimetry estimated normal organ absorbed radiation doses are not affected by prior therapy with rituximab."
Wiseman G.A. et al. *Clin. Cancer Res.* 5(Suppl.): 3281s-3286s, 1999. "Radioimmunotherapy of relapsed non-Hodgkin's lymphoma with Zevalin, a $^{90}$Y-labeled anti-CD20 monoclonal antibody."
Wiseman G.A. et al. *I. J. Oncol. Biol. Phys.* 42(1 Suppl .): 130, abst. No. 11, 1998. "IDEC-Y2B8 ($^{90}$yttrium ibritumomab tiuxetan) radioimmunotherapy safety results in relapsed or chemotherapy refractory non-Hodgkin's lymphoma patients treated at reduced doses because of pre-existing thrombocytopenia."
Wiseman G.A. et al. *I. J. Oncol. Biol. Phys.* 45(3 Suppl .): 390, abst. No. 2217, 1999. "IDEC-Y2B8 (90yttrium ibritumomab tiuxetan) radioimmunotherapy safety results in relapsed or chemotherapy refractory non-Hodgkin's lymphoma patients treated at reduced doses because of pre-existing thrombocytopenia."
Wiseman G.A. et al. *J. Nucl Med.* 38(5 Suppl.): 251, abst. No. 1062, 1997. "Y-90 anti-CD20 monoclonal antibody (IDEC-Y2B8) dosimetry calculated from In-111 anti-CD20 in patients with low and intermediate grade B-cell non-Hodgkin's lymphoma."
Wiseman G.A. et al. *J. Nucl Med.* 39(5 Suppl.): 185P, abst. No. 836, 1998. "Whole-body gamma camera image quantification from multiple camera types for radioisotope therapy dosimetry."
Wiseman G.A. et al. *J. Nucl Med.* 39(5 Suppl.): 69P, abst. No. 267, 1998. "Non-Hodgkin's lymphoma tumor and bone marrow radiation doses from radioimmunotherapy with IDEC-Y2B8 yttrium-90 anti-CD20 monoclonal antibody."
Wiseman G.A. et al. *J. Nucl Med.* 40(1 Suppl .): 64P, abst. No. 260, 1999. "Final dosimetry results of IDEC-Y2B8 phase I/II $^{90}$yttrium radioimmunotherapy trial in non-Hodgkin's lymphoma (NHL)."
Wiseman G.A. et al. *Proc. Amer. Soc. Clin. Oncol.* 18: 4a, abst. No. 13, 1999. "Therapeutic index of IDEC-Y2B8 radioimmunotherapy: up to 850 fold greater radiation dose to tumor than normal organs."
Witherspoon R.P. et al. *Semin. Hematol.* 21(1): 2-10, 1984, "Immunologic reconstitution after human marrow grafting".
Witzig T. et al. *Blood* 90(10 Suppl. 1): 586a, abst. No. 2606, 1997, "IDEC-Y2B8 90yttrium anti-CD20 radioimmunotherapy of relapsed non-Hodgkin's lymphoma (NHL): interim results of a phase I/II trial".
Witzig T. et al. *Blood* 92(10 Suppl. 1): 417a, abst. No. 1722, Nov. 1998, "IDEC-Y2B8 radioimmunotherapy: responses in patients with splenomegaly".
Witzig T.E. et al. *Am. J. Clin. Pathol.* 101: 312-17, 1994, "Measurement of the intensity of cell surface antigen expression in B-cell chronic lymphocytic leukemia".
Witzig T.E. et al. *Blood* 94(10 Suppl. 1): 631a, abst. No. 2805, 1999, "Prospective randomized controlled study of Zevalin™ (IDEC-Y2B8) radioimmunotherapy compared to rituximab immunotherapy for B-cell NHL: report of interim results".
Witzig T.E. et al. *Blood* 94(10 Suppl. 1): 92a, abst. No. 400, 1999, "Reduced-dose Zevalin™ radioimmunotherapy for relapsed or refractory B-cell non-Hodgkin's lymphoma (NHL) patients with pre-existing thrombocytopenia: report of interim results of a phase II trial".
Witzig T.E. et al. *J. Clin. Oncol.* 17(12): 3793-3803, 1999, "Phase I/II trial of IDEC-Y2B8 radioimmunotherapy for treatment of relapsed or refractory CD20(+) B-cell non-Hodgkin's lymphoma".
Witzig T.E. et al. *J. Clin. Oncol.* 20(15): 3262-69, 2002, "Treatment with ibritumomab tiuxetan radioimmunotherapy in patients with rituximab-refractory follicular non-Hodgkin's lymphoma".
Witzig T.E. et al. *J. Clin. Oncol.* 20: 2453-63, 2002, "Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma".
Witzig T.E. et al. *J. Immunother.* 21(6): 463, abst. No. 2805, 1998, "IDEC-Y2B8 radioimmunotherapy of relapsed or refractory non-Hodgkin's lymphoma".
Witzig T.E. et al., *Proc. Amer. Soc. Clin. Oncol.* 18: 41a, abst. No. 152, 1999. "Commonly used response criteria for non-Hodgkin's lymphoma (NHL) applied to IDEC-Y2B8 radioimmunotherapy trial: importance of "normal" lymph node size".
Yakoub-Agha et a., Bone Marrow Transplant 30(4): 229-34 (2002), "Allogeneic bone marrow transplantation in patients with follicular lymphoma: a single center study".
Yang H. et al., *Am. J. Hematol.* 62: 247-50, 1999, "Tumor lysis syndrome occurring after the administration of rituximab in lymphoproliferative disorders: high-grade non-Hodgkin's lymphoma and chronic lymphocytic leukemia".
Yokota S. et al., *Cancer Res.* 50: 32-37, 1990, "Synergistic potentiation of in vivo antitumor activity of anti-human T-leukemia immunotoxins by recombinant a-interferon and daunorubicin".
Zhou X. et al. *Chinese Pharm. J.* 30(8): 453-54, 1995, "Application of cytokine therapy in tumor treatment", (English translation of Abstract provided.).
"Biological Therapy for Cancer Treatment", Stanford Cancer Center, https://web.archive.org/web/20131617382400/http://cancer.stanford.edu/information/cancerTreatment/methods/biological.html, 2009 (archived Jun. 17, 2013), pp. 1-8 (Retrieved Dec. 22, 2014).
"NCI—Cooperative Group—Industry Relationship Guidelines", updated May 29, 2008 http://ctep.cancer.gov/industrycollaborations2/guidelines.htm, retrieved Aug. 25, 2015, pp. 1-3.
Aisenberg AC, "Coherent view of non-Hodgkin's lymphoma." J Clin Oncol., 1995, vol. 13, pp. 2656-2675.
Al-Ismail, "Combination chemotherapy Including Epirubicin for the Management of Non-Hodgkin's Lymphoma", European J. Cancer and Clinical Oncology, 1987, vol. 23, pp. 1379-1384.

(56) References Cited

OTHER PUBLICATIONS

Amendment and Reply under 35 CFR §1.111 filed Aug. 25, 2010, in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-16.
Amendment and Response to Restriction Requirement filed Jan. 29, 2010 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-9.
Amendment Responsive to Examiner's Request filed Oct. 28, 2011 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-8.
Applicant's Remarks/ Arguments filed Jun. 6, 2011 in U.S. Appl. No. 11/840,956 (Antonio J. Grillo-Lopez, Combination Therapies for B-Cell Lymphomas Comprising Administration of Anti-CD20 Antibody, filed Aug. 18, 2007) pp. 19-35.
Applicant's Remarks/Arguments filed May 22, 2012 with USPTO in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-8.
Aviles et al., "Interferon Alpha 2b as Maintenance Therapy in Low Grade Malignant Lymphoma Improves Duration of Remission and Survival", Leukemia and Lymphoma, 1996, vol. 20, pp. 495-499.
Aviles et al., "Maintenance therapy with interferon alfa 2b in patients with diffuse large cell lymphoma", Investigational New Drugs, 1992, vol. 10, pp. 351-355.
Aviles, A., "The role of Interferon as Maintenance Therapy in Malignant Lymphoma", Medical Oncology, 1997, vol. 14, pp. 153-157.
Biogen's Patent Owner Preliminary Response filed Apr. 15, 2015 in Response to Petition Inter Partes Review of U.S. Pat. No. 8,329,172 dated Dec. 15, 2014 (U.S. Appl. No. 11/840,956, Antonio J. Grillo-Lopez, Combination Therapies for B-Cell Lymphomas Comprising Administration of Anti-CD20 Antibody, filed Aug. 18, 2007) pp. 1-69.
Biological Therapies: Using the Immune System to Treat Cancer, National Cancer Institute, http://web.archive.org/web/19980216091909/http://cancernet.nci.nih.gov/clinpdq/therapy/Biological_Therapies:_Using_the_Immune_System_To_Treat_Cancer.html (last modified Sep. 1995, archived Feb. 16, 1998) pp. 1-5 (retrieved Apr. 8, 2014).
Blackwelder, William C., "'Proving the Null Hypothesis' in Clinical Trials", Controlled Clinical Trials, 1982, vol. 3, pp. 345-353.
Cabanillas et. al., "Clinical, Biologic, and Histologic Features of Late Relapses in Diffuse Large Cell Lymphoma", Blood, Feb. 1992, vol. 79, No. 4, pp. 1024-1028.
Carlson, R. "Rituximab plus CHOP: a new approach for non-Hodgkin's lymphoma?" Inpharma No. 1116:7-8 (Dec. 6, 1997) (Chemotherapy Foundation Symposium XV, New York, US, Nov. 1997).
Chisesi et. al., "Randomized Study of Chlorambucil (CB) Compared to Interferon (Alfa-2b) Combined with CB in Low-Grade Non-Hodgkin's Lymphoma: An interim report of a randomized study", Eur. J. Cancer, 1991, vol. 27, Supp. 4, pp. S31-S33.
Clendeninn, N.J., et. al., "Phase I/II trials of CAMPATH-1H, a humanized anti-lymphocyte monoclonal antibody (MoAb), in non-Hodgkin's lymphoma (NHL) and chronic lymphocytic leukemia (CLL).", Blood, Nov. 1992, vol. 80, No. 10, Supplement 1, Abstract #624, p. 158a.
Clinical Review of BLA Reference No. BLA 97/0260 and BLA 97/0244, pp. 1-40 with cover page signed: Nov. 1997; the source is available on the Internet (as of Nov. 28, 2013) at the following (URL): http://www.fda.gov/downloads/Drugs/DevelopmentApprovalProcess/HowDrugsareDevelopedandApproved/ApprovalApplications/TherapeuticBiologicApplications/ucm113330.pdf.
Clinical Trials (PDQ®); "Phase III randomized Study of CHOP (Cyclophosphamide, Doxorubicin, Vincristine, and Prednisone) With or Without Rituximab in Older Patients With Diffuse Mixed, Diffuse Large, or Immunoblastic Large Cell Non-Hodgkin's Lymphoma"; retrieved Jan. 17, 2013; pp. 1-7 http://www.cancer.gov/clinicaltrials/search/view?cdrid=65935&version=HealthProfessional.
ClinicalTrials.gov report on the NCT00003204 (ECOG 1496) Clinical Trial (Jan. 27, 2014) http://clinicaltrials.gov/show/NCT00003204 pp. 1-5 (retrieved Dec. 2, 2014).
Coiffier, B., "What treatment for elderly patients with aggressive lymphoma?", Annals of Oncology, 1994, vol. 5, pp. 873-875.
Dana et. al., "A Randomized Study of Alpha-Interferon Consolidation in Patients with Low-Grade Lymphoma Who Have Responded to Pro-Mace-Mopp (Day 1-8) (SWOG 8809)", Proceedings of ASCO, May 16-19, 1998, vol. 17, Abstract 10, p. 3a.
Decision Denying Institution of Inter Partes Review of U.S. Pat. No. 8,329,172 dated Jul. 13, 2015 (U.S. Appl. No. 11/840,956, Antonio J. Grillo-Lopez, Combination Therapies for B-Cell Lymphomas Comprising Administration of Anti-CD20 Antibody, filed Aug. 18, 2007) pp. 1-35.
Declaration of Michael J. Grossbard, M.D., in Support of the Petition for Inter Partes Review of U.S. Pat. No. 8,329,172 (U.S. Appl. No. 11/840,956, Antonio Grillo-Lopez, filed Aug. 18, 2007), dated Dec. 5, 2014 pp. 1-107.
Dillman -et al., "Therapy of chronic lymphocytic leukemia and cutaneous T-cell lymphoma with T101 monoclonal antibody." J Clin Oncol, 1984, vol. 2, pp. 881-891.
Dixon, et. al., "Effect of Age on Therapeutic Outcome in Advanced Diffuse Histiocytic Lymphoma: The Southwest Oncology Group Experience", Mar. 1986, vol. 4, No. 3, pp. 295-305.
Documents from European Oppositions pertaining to EP Application No. 08005921.5 (Antonio J. Grillo-Lopez, Combination Therapies for B-Cell Lymphomas Comprising Administration of Anti-CD20 Antibody, filed Aug. 11, 1999) (Patent No. EP 1974747), pp. 1-52.
ECOG E1496 Trial Results "Non-Progressing Low-grade NHL after CVP-Rituxan® (Rituximab)", Internet Archive, Wayback Machine, Originally Posted Sep. 25, 2008, pp. 1-5, (Retrieved Oct. 14, 2014) https://secure-web.cisco.com/1B2U3jOtb8QOJNLQGvSxJia-M2nvnbtabJUaFOTicFseG--vgr6XlzX0SKoku-oNvzU0Wy30uzOQ8soECOu8WwpRqt9Fxzxkoll_y_4voe2AmM9qyHNLKQrMuc_ZNIPPr718_AnmuaCegoojIE3DYgide44BddInvz6PyjGkSMAKhepiFJRo_FsbJ4sXMkEk0jSZmHoKCuYXXxYBznkpyLHFKEztuNJ1-khQP_1hzLj2T9csm0hG15ka825qQQlq5lgxX-8vqnyxnQ9PKVwtU9CdvQSneMRAmZr6ZEJRYIfewuhXO-7Pu9hCDKyU1R5Yz2I/https%3A%2F%2Fweb.archive.org%2Fweb%2F20080925225303%2Fhttp%3A%2F%2Fwww.rituxan.com%2Flymphoma%2Fhep%2Findications%2FE1496%2Findex_m.
ECOG E1496, Activation of Protocol E1496, Randomized Phase III Study in Low Grade Lymphoma Comparing Cyclophosphamide/Fludarabine to Standard Therapy Followed by Maintenance Anti-CD20 Antibody, Activation Date: Mar. 19, 1998 pp. 1-47.
ECOG E4494, Activation of Protocol E4494, a Phase III Trial of Chop versus Chop and Chimeric Anti-CD20 Monoclonal Antibody (IDEC-C2B8) in Older Patients with Diffuse Mixed, Diffuse Large Cell and Immunoblastic Large Cell Histology Non-Hodgkin's Lymphoma, Activation Date: Dec. 12, 1997 pp. 1-61.
ECOG Institutions by Name, http://web.archive.org/web/19980519084032/http://ecog.dfci.harvard.edu/~ecogdba/general/insts_byname.html (archived May 19, 1998) pp. 1-10 (retrieved Dec. 4, 2014).
FDA Clinical Review of Rituximab dated Sep. 29, 2006, pp. 1-110.
Fisher et al. "Comparison of a standard regimen (CHOP) with three intensive chemotherapy regimens for advanced non-Hodgkin's lymphoma", The New England Journal of Medicine 328(14):1002-1006 (Apr. 8, 1993).
Foon et. al., "Lymphomas", Williams Hematology, 5th edition, Ch. 111, Part ix, Beutler, Lichtman, Coller, & Kipps, McGraw-Hill, Inc., 1995, pp. 1076-1096.
Foon KA et al., "Effects of monoclonal antibody therapy in patients with chronic lymphocytic leukemia." Blood, 1984, vol. 64, pp. 1085-1093.

(56) References Cited

OTHER PUBLICATIONS

Gallagher CJ et al., "Follicular lymphoma: Prognostic factors for response and survival.", 1986, J Clin Oncol, vol. 4, pp. 1470-1480.
Ghielmini et al., "Prolonged treatment with rituximab in patients with follicular lymphoma significantly increases event-free survival and response duration compared with the standard weekly X4 schedule", Blood, 2004, vol. 103, No. 12, pp. 4416-4423.
Gisselbrecht et. al., "Treatment of low-grade non-Hodgkin's lymphomas", Non-Hodgkin's Lymphoma, Solal-Céligny, Brousse, Reyes, Gisselbrecht & Coiffier, Manson Publishing Ltd., 1993, pp. 317-336.
Gisselbrecht, et. al., "Rituximab maintenance therapy after autologous stem-cell transplantation in patients with relapsed CD20(+) diffuse large B-cell lymphoma: final analysis of the collaborative trial in relapsed aggressive lymphoma", J. Clin. Oncol., Dec. 2012, vol. 30, No. 36, pp. 4462-4469.
Gottlieb et al. "Chemotherapy of malignant lymphoma with adriamycin", Cancer Research 33:3024-3028 (Nov. 1973).
Gribben JG et al., "Detection of residual lymphoma cells by polymerase chain reaction in peripheral blood is significantly less predictive for relapse than detection in bone marrow." Blood, 1994, vol. 83, pp. 3800-3807.
Grillo-López, AJ "The First Antibody Therapy for Cancer: a Personal Experience", Expert Review of Anticancer Therapy Retrospective, 2013, vol. 13, No. 4, pp. 399-406.
Gupta and Lister, "Current Management of Follicular Lymphoma", Current Opinion in Oncology, 1996, vol. 8, pp. 360-365.
Hainsworth et al. "Rituximab as First-Line and Maintenance Therapy for Patients With Indolent Non-Hodgkin's Lymphoma", J. Clinical Oncology, 2002, vol. 20, pp. 4261-4267.
Haioun, et. al., "Survival Benefit of High-Dose Therapy in Poor-Risk Aggressive Non-Hodgkin's Lymphoma Final Analysis of the Prospective LNH87-2 Protocol—A Groupe d'Etude des Lymphomes de l'Adute Study", Aug. 2000, vol. 18, No. 16, pp. 3025-3030.
Hickish et al., "Molecular monitoring of low grade non-Hodgkin's lymphoma by gene amplification", Br. J. Cancer, 1991, vol. 64, pp. 1161-1163.
Hiddemann et al., "New Aspects in the Treatment of Advanced Low-Grade Non-Hodgkin's Lymphomas: Prednimustine/Mitoxantrone Versus Cyclophosphamide/Vincristine/Prednisone Followed by Interferon Alfa Versus Observation Only—A Preliminary Update of the German Low-Grade Lymphoma Study Group", Seminars in Hematology, 1994, vol. 31, No. 2, Suppl 3, pp. 32-35.
Hoerni et al., "Maintenance Immunotherapy with BCG in Non-Hodgkin's Malignant Lymphomas: a Progress Report of a Randomized Trial", Recent Results in Cancer Research, 1982, vol. 80, pp. 92-97.
Hoerni et al., "Successful Maintenance Immunotherapy by BCG of Non-Hodgkin's Malignant Lymphomas: Results of a Controlled Trial", British J. Haematology, 1979, vol. 42, pp. 507-514.
Information Disclosure Statement From PTO-1449 considered by emainer on May 10, 2010 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-31.
International Non-Hodgkin's Lymphoma Prognostic Factors Project, "A Predictive Model for Aggressive Non-Hodgkin's Lymphoma," N Engl. J Med 329(14): 987-994 (1993).
Jones et al., "Improved Complete Remission Rates and Survival for Patients with Large Cell Lymphoma Treated with Chemoimmunotherapy", Cancer, 1983, vol. 51, pp. 1083-1090.
Kaplan EL et al., "Nonparametric estimation from incomplete observations." J Am Stat Assoc, 1958, vol. 53, pp. 457-481.
Khan et al., "A phase 2 study of rituximab in combination with recombinant interleukin-2 for rituximab-refractory indolent non-Hodgkin's lymphoma," Clin. Cancer Res. 12(23): 7046-53 (2006).
Kohler and Milstein, "Derivation of Specific Antibody-Producing Tissue culture and Tumor Lines by Cell Fusion", European J. Immunology, 1976, vol. 6, pp. 511-519.

Kwak et. al., "Biological response modifiers, The Non-Hodgkin's Lymphomas", 2nd edition, Ch. 32, Ian T. MaGrath, Arnold, 1997, pp. 699-714.
Leonard et. al., "Monoclonal Antibody Therapy of Lymphoma", American Cancer Society Atlas of Clinical Oncology Malignant Lymphomas, Ch. 18, Michael L. Grossbard, BC Decker Inc. 2002, pp. 301-315.
LoBuglio AF et al., "Mouse/human chimeric monoclonal antibody in man: Kinetics and Immune response." PNAS, 1989, vol. 86, pp. 4220-4224.
Lopez-Guillermo A et al., "The molecular breakpoint site of bcl-2 gene has prognostic importance in indolent follicular lymphoma.", Blood, Nov. 1996, vol. 88, No. 10, Suppl 1 Part 1 of 2, Abstract 1162, p. 293a.
Lopez-Guillermo et al. "The clinical significance of molecular response in indolent follicular lymphomas", Blood, Apr. 1998, vol. 91, No. 8, pp. 2955-2960.
McLaughlin et al., "Management of Patients with Nodular Lymphoma", UT M.D. Anderson Clinical Conference on Cancer, 1984, vol. 27, pp. 301-312.
McLaughlin p. et al., "Fludarabine phosphate in lymphoma: an important new therapeutic agent" in Advances in Lymphoma Research, Boston, MA, Cabanillas F, Rodriguez, MA, Kluwer Academic Publishers, 1996, pp. 3-14.
McLaughlin P. et al. J. Clin Oncol. 16(8): 2825-2833, Aug. 1998. "Rituximab chimeric-anti-CD20 monoclonal antibody therapy for relapsed indolent lymphoma. half of patients respond to a four-dose treatment program" (Previously submitted); with e-mail from publisher Glenn Landis dated Nov. 5, 2012, 1 page, stating the official publication date thereof was Aug. 1, 1998.
McNeil, C. "Non-Hodgkin's Lymphoma Trials in Elderly Look Beyond CHOP", Journal of the National Cancer Institute, Feb. 18, 1998, vol. 90, No. 4, pp. 266-267.
Meyer, et. al., "Randomized Phase II Comparison of Standard Chop with Weekly CHOP in Elderly Patients with Non-Hodgkin's Lymphoma", Journal of Clinical Oncology, Sep. 1995, vol. 13, No. 9, pp. 2386-2393.
Mueller BM et al., "Enhancement of antibody-dependent cytotoxicity with a chimeric anti-GD2 antibody." J Immunol, 1990, vol. 144, pp. 1382-1386.
Notice of Allowability dated Jun. 26, 2012 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-2.
Office Action mailed by the USPTO dated Feb. 29, 2012 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-12.
Office Restriction Requirement mailed Oct. 15, 2009 in U.S. Appl. No. 11/840,956 (Antonio J. Grillo-Lopez, Combination Therapies for B-Cell Lymphomas Comprising Administration of Anti-CD20 Antibody, filed Aug. 18, 2007) pp. 1-5.
Official Action mailed by the Uspto dated May 11, 2010 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-8.
Patent Owner's Updated Mandatory Notices in Petition for Inter Partes Review of U.S. Pat. No. 8,329,172 dated May 11, 2015 (U.S. Appl. No. 11/840,956, Antonio J. Grillo-Lopez, Combination Therapies for B-Cell Lymphomas Comprising Administration of Anti-CD20 Antibody, filed Aug. 18, 2007) pp. 1-4.
PDQ—NCI's Comprehensive Cancer Database, http://web.archive.org/web/19980116194104/http://cancernet.nci.nih.gov/pdq.htm (archived Jan. 16, 1998) pp. 1-2 (retrieved Dec. 4, 2014).
Peterson et. al., "Cyclophosphamide versus cyclophosphamide plus interferon alfa-2b in follicular low-grade lymphomas: an intergroup phase III trial (CALGB 8691 and EST 7486)", Proceedings of ASCO, May 17-20, 1997, vol. 16, Abstract 48, p. 14a.
Petition for Inter Partes Review of U.S. Pat. No. 8,329,172 (U.S. Appl. No. 11/840,956, Antonio J. Grillo-Lopez, Combination Therapies for B-Cell Lymphomas Comprising Administration of Anti-CD20 Antibody, filed Aug. 18, 2007) dated Dec. 15, 2014 pp. 1-76.

(56) References Cited

OTHER PUBLICATIONS

Petitioner's Request for Rehearing on the Institution Decision in Inter Partes Review of U.S. Pat. No. 8,329,172 dated Dec. 15, 2014 (U.S. Appl. No. 11/840,956, Antonio Grillo-Lopez, Combination Therapies for B-Cell Lymphomas Comprising Administration of Anti-CD20 Antibody, filed Aug. 18, 2007) pp. 1-18.
Petryk et.al., "Indolent B-Cell Lymphomas", American Cancer Society Atlas of Clinical Oncology Malignant Lymphomas, Ch. 6, Michael L. Grossbard, BC Decker Inc. 2002, pp. 94-111.
Pettengell, et. al., "Randomised study of rituximab in patients with relapsed or resistant follicular lymphoma prior to high-dose therapy as in vivo purging and to maintain remission following high-dose therapy", J. Clin. Oncol., 2010, vol. 18, Supp. 10, abstr. 8005, retrieved from http://meetinglibrary.asco.org/print/57934 on Feb. 10, 2016 (2 pages).
Pettengell, Ruth (on behalf of the EBMT Lymphoma Working Party), "Randomised study of rituximab (MabThera) in patients with relapsed or resistant follicular lymphoma prior to high dose therapy as in vivo purging and to maintain remission (NCT00005589)", slides presented by the European Group for Blood and Marrow Transplantation at the 2010 ASCO Annual Meeting (20 pages).
Piro LD, "Cladribine in the treatment of low-grade non-Hodgkin's lymphoma." Semin Hematol, 1996, vol. 33, No. 1, Suppl 1, pp. 34-39.
Pott-Hoeck C. et al., "Purine analogs in the treatment of low-grade lymphomas and chronic lymphocytic leukemias." Ann Oncol, 1995, vol. 6, pp. 421-433.
Poynton CH et al., "Adverse reactions to Campath-1H monoclonal antibody." Lancet , 1993, vol. 341, p. 1037.
Preliminary Amendment filed Oct. 31, 2007 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-5.
Prescribing information for Rituxan (Rituximab), Initial US Approval Nov. 1997, revised Aug. 2014 (39 pages).
Public Hearing Transcript, Biological Response Modifiers Advisory Committee, Center for Biological Evaluation and Research, Department of Health and Human Services—Food and Drug Administration, nineteenth meeting Jul. 25, 1997, pp. 1-201.
Ravaud et al., "Adjuvant Bacillus Calmette-Guerin Therapy in Non-Hodgkin's Malignant Lymphomas: Long-Term Results of a Randomized Trial in a Single Institution", J. Clinical Oncology, 1990, vol. 8, pp. 608-614.
Rituxan® (Rituximab) Draft Labeling Text, U.S. BL 103705/5230 Amendment: Rituxan®(Rituximab)—Genentech, Inc. Sep. 29, 2006, pp. 1-46.
Rituxan® (Rituximab) Labeling Text, U.S. BL 103705 Supplemental Amendment: Rituxan Rheumatoid Arthritis—Genentech , Inc. Feb. 2006, pp. 1-53.
Ritz J et al., "Serotherapy of acute lymphoblastic leukemia with monoclonal antibody." Blood, 1981, vol. 58, pp. 141-152.
Rohatiner et. al., "Follicular Lymphoma, The Non-Hodgkin's Lymphomas", $2^{nd}$ edition, Ch. 41, Ian T. MaGrath, Arnold, 1997, pp. 867-895.
Rohatiner et. al., "Meta-Analysis to Evaluate the Role of Interferon in Follicular Lymphoma," J. Clinical Oncology, Apr. 2005, vol. 23, No. 10, pp. 2215-2223.
Schein et. al., "Non-Hodgkin's Lymphoma: Patterns of Relapse from Complete Remission After Combination Chemotherapy", Cancer, 1975, vol. 35, pp. 354-357.
Sonneveld, et. al., "Comparison of Doxorubicin and Mitoxantrone in the Treatment of Elderly Patients with Advanced Diffuse Non-Hodgkin's Lymphoma Using CHOP Versus CNOP Chemotherapy", Journal of Clinical Oncology, Oct. 1995, vol. 13, No. 10, pp. 2530-2539.
Tedder TF et al., "CD20: A regulator of cell-cycle progression of B lymphocytes." Immunol Today, 1994, vol. 15, pp. 450-454.
United States Department of Health and Human Services, Food and Drug Administration, "Guidance for Industry: Distributing Scientific and Medical Publications on Unapproved New Uses—Recommended Practices", Revised Draft Guidance, Feb. 2014, pp. 1-17.
Unterhalt et al., "Significant Prolongation of Disease Free Survival in Advanced Low Grade Non Hodgkin's Lymphomas (NHL) by Interferon Alpha Maintenance: International Conference on Malignant Lymphoma, Jun. 5-8, 1996, Lugano, Switzerland", Annals of Oncology, 1996, vol. 7, Supplement 3, pg. 229.
Unterhalt, et. al., "Long Term Interferon Alpha Maintenance Prolongs Remission Duration in Advanced Low Grade Lymphomas and is Related to the Efficacy of Initial Cytoreductive Chemotherapy", Blood, Nov. 1996, vol. 88, No. 10, Suppl. 1, Abstract 1801, pp. 453a.
Van Oers et al., "Rituximab maintenance improves clinical outcome of relapsed/resistant follicular non-Hodgkin lymphoma in patients both with and without rituximab during induction: results of a prospective randomized phase 3 intergroup trial", Blood, 2006, vol. 108, pp. 3295-3301.
Vose, et. al., "Long-term update of a phase II study of rituximab in combination with previously untreated, aggressive non-Hodgkin's lymphoma", Leukemia & Lymphoma, Nov. 2005, vol. 46, No. 11, pp. 1569-1573.
Zhou L-J et al., "CD20 Workshop Panel Report" in Schlossman SF. Boumsell L., Gilks W., et al. (eds): Leucocyte Typing V (White Cell Differentiation Antigens. Proceedings of the Fifth International Workshop and Conference Held in Boston, USA Nov. 3-7, 1993) Oxford, United Kingdom, Oxford University, 1995, vol. 1, pp. 511-514.
Archived ECOG website, Jun. 8, 1998, retrieved from parent URL http://web.archive.org/web/19981212013740/http:/ecog.dfci. harvard.edu on Mar. 19, 2015 and Mar. 20, 2015, pp. 1-109.
Czuczman, Myron, presentation titled "IDEC-C2B8/CHOP Chemoimmunotherapy in Patients With Low-Grade Lymphoma: Clinical and BCL-2 (PCR) Final Results" presented by Dr. Myron Czuczman at the 38th Annual Meeting of the American Society of Hematology in Orlando, Florida on Dec. 6-10, 1996 (15 pages).
Grillo-Lopez, et. al., presentation titled "IDEC-C2B8 Rituxan (rituximab)" presented at Biological Response Modifiers Committee Review in Bethesda, Maryland on Jul. 25, 1997 (77 pages).
McLaughlin, Peter, presentation titled "IDEC-C2B8 Anti-CD20 Antibody: Final Report on a Phase III Pivotal Trial in Patients (PTS) With Relapsed Low-Grade or Follicular Lymphoma (LG/F NHL)" presented at the 38th Annual Meeting of the American Society of Hematology in Orlando, Florida on Dec. 6-10, 1996 (21 pages).
McLaughlin, Peter, presentation titled "Pharmacokinetics (PK) and Pharmacodynamics (PD) of the Anti-CD20 Antibody (MAB) IDEC-C288 in Patients (PTS) With Relapsed Low-Grade or Follicular Lymphoma (LG/F NHL)" presented at the 38th Annual Meeting of the American Society of Hematology in Orlando, Florida on Dec. 6-10, 1996 (21 pages).
National Cancer Institute: Surveillance, Epidemiology, and End Results Program, "SEER Stat Fact Sheets: Non-Hodgkin Lymphoma", http://seer.cancer.gov/statfacts/html/nhl.html , Apr. 2014, pp. 19 (retrieved Dec. 2, 2014).
Rituxan® (Rituximab) ECOG 1496 Trial for Low-grade or Follicular Non-Hodgkin's Lymphoma, 2012, http://www.rituxan.com/hem/hcp/non-hodgkin/post-induction/ecog/index.html; pp. 1-3; (Retrieved 2012); Trial Design Published in Hochster et al., J. Clin. Oncol. 2009; 27:1607-1614.
Vose et. al., "Diagnosis and Treatment of Non-Hodgkin's Lymphoma of Adults", Neoplastic Diseases of the Blood, $3^{rd}$ edition, Ch. 44, Wiernik, Canellos, Dutcher, & Kyle, Churchill Livingstone, 1996, pp. 907-924.

\* cited by examiner

TREATMENT OF DIFFUSE LARGE-CELL LYMPHOMA WITH ANTI-CD20 ANTIBODY

CROSS REFERENCE TO RELATED APPLICATIONS

This application is a continuation application of U.S. patent application Ser. No. 14/045,375 filed Oct. 3, 2013, which is a divisional of U.S. application Ser. No. 09/628,187 filed Jul. 28, 2000, now U.S. Pat. No. 8,557,244, issued Oct. 15, 2013, which claims priority under 35 U.S.C. Section 119(e) and the benefit of U.S. Provisional Application Ser. No. 60/148,286 filed Aug. 11, 1999, the entire disclosures of which are incorporated herein by reference in their entireties.

FIELD OF THE INVENTION

The present invention concerns methods of treating intermediate- and high-grade non-Hodgkin's lymphomas, and lymphomas associated with a high level of bone marrow involvement with anti-CD20 monoclonal antibodies and fragments thereof.

BACKGROUND OF THE INVENTION

Non-Hodgkin's lymphoma is characterized by the malignant growth of B lymphocytes. According to the American Cancer Society, an estimated 54,000 new cases will be diagnosed, 65% of which will be classified as intermediate- or high-grade lymphoma. Patients diagnosed with intermediate-grade lymphoma have an average survival rate of 2-5 years, and patients diagnosed with high-grade lymphoma survive an average of 6 months to 2 years after diagnosis.

Intermediate- and high-grade lymphomas are much more aggressive at the time of diagnosis than are low-grade lymphomas, where patients may survive an average of 5-7 years with conventional therapies. Intermediate- and high-grade lymphomas are often characterized by large extranodal bulky tumors and a large number of circulating cancer cells, which often infiltrate the bone marrow of the patient.

Conventional therapies have included chemotherapy and radiation, possibly accompanied by either autologous or allogeneic bone marrow or stem cell transplantation if a suitable donor is available, and if the bone marrow contains too many tumor cells upon harvesting. While patients often respond to conventional therapies, they usually relapse within several months.

A relatively new approach to treating non-Hodgkin's lymphoma has been to treat patients with a monoclonal antibody directed to a protein on the surface of cancerous B cells. The antibody may be conjugated to a toxin or radiolabel thereby affecting cell death after binding. Alternatively, an antibody may be engineered with human constant regions such that human antibody effector mechanisms are generated upon antibody binding which result in apoptosis or death of the cell.

One antibody currently being investigated for the treatment of intermediate- and high-grade lymphomas is ONCOLYM® ($^{131}$I-Lym-1) (Techniclone Corp.), which is a murine IgG2a monoclonal antibody which recognizes the HLA-Drl 0 protein which is present on the surface of over 80% of lymphoma cells. Only 2% of normal B cells (noncancerous) express the HLA-Drl 0 molecule. ONCOLYM® IgG2a monoclonal antibody is conjugated to a Iodine-[131] ($^{131}$I), a radioactive isotope of iodine which emits beta irradiation for a distance of several millimeters, and is thereby thought to be an effective approach to targeting the outer rim of tumors and halting the progression of bulky disease However, a potential disadvantage in using ONCOLYM® IgG2a monoclonal antibody in advanced forms of non-Hodgkin's lymphoma is that such lymphomas are often characterized by bone marrow involvement. Thus, administration of a radiolabeled antibody to such patients often results in unwanted myelosuppression and damage to healthy progenitor cells.

It would be advantageous if alternative therapies and other monoclonal antibodies could be administered to patients with intermediate- and high-grade lymphomas which circumvent some of the deficiencies associated with current treatments and decrease the frequency of relapse.

SUMMARY OF THE INVENTION

The present invention concerns the use of anti-CD20 antibodies for the treatment of intermediate- and high-grade lymphomas, particularly those which are characterized by bone marrow involvement and bulky disease. In particular, the present inventors have surprisingly found that rituximab, a chimeric anti-CD20 antibody already approved for the treatment of low-grade follicular non-Hodgkin's lymphoma, may be effective to treat more aggressive lymphomas as well.

DETAILED DESCRIPTION OF THE INVENTION

The present invention relates to methods for treating or alleviating the symptoms of intermediate- or high-grade non-Hodgkin's lymphoma, or other lymphomas associated with a high degree of bone marrow involvement, comprising administering to a patient a therapeutically effective amount of an anti-CD20 antibody or other lymphoma cell depleting antibody, e.g. anti-CD19 and anti-CD22 antibodies, or a therapeutically effective fragment thereof. The present invention also includes administering anti-CD20 antibodies, or other lymphoma cell depleting antibodies, as part of a transplant regimen (autologous bone marrow transplant or allogeneic bone marrow transplant or peripheral blood stem cell transplant) to improve the survival of transplant recipients.

Therapeutically effective antibody "fragments" refers to any portion of or derivative of an antibody that is capable of delivering substantially the same therapeutic effect as the whole antibody when administered to a patient having intermediate- or high-grade non-Hodgkin's lymphoma (NHL), or when used as part of a transplant regimen.

As the understanding of lymphoma improves and new histopathologic variations are diagnosed, new classification systems for the different types of lymphoma have emerged. In general, for the purposes of the methods described herein, intermediate- and high-grade lymphomas are defined as those designated in the "Working Formulation" established in 1982. This system includes as intermediate-grade lymphomas follicular large cell (FL), diffuse small cleaved cell (DSC), diffuse mixed small and large cell (DM), and diffuse large cell, cleaved or noncleaved (DL). As high-grade lymphomas, the system recognizes immunoblastic large cell (IBL), lymphoblastic, convoluted or nonconvoluted (LL), and small noncleaved cell, Burkitt's or non-Burkitt's (SNC).

Several classification systems have emerged since the proposed Working Formulation. For instance, a recent classification system proposed by European and American pathologists is called the Revised European American Lymphoma (REAL) Classification. Although this classification system does not use the terms "intermediate-" and "high-grade" NHL, it will be understood by those of skill in the art which lymphomas are typically characterized as "intermediate-" and "high-grade." For instance, "mantle cell lymphoma" as defined in the REAL classification system may appear as both indolent and more aggressive forms, and depending on the severity may be classified as an intermediate- or high-grade lymphoma.

For instance, the U.S. National Cancer Institute (NCI) has in turn divided some of the REAL classes into more clinically useful "indolent" or "aggressive" lymphoma designations. "Aggressive" lymphomas include diffuse mixed and large cell lymphoma, Burkitt's lymphoma/diffuse small non-cleaved cell lymphoma, Lymphoblastic lymphoma, Mantle cell lymphoma and AIDS-related lymphoma. These lymphomas would therefore be considered at least "intermediate" or "high-grade," and would therefore benefit from the therapeutic methods of the present invention.

While strict classifications of some lymphomas may be difficult, the lymphomas treatable by the present invention are generally characterized by a high number of circulating B cells, possible bone marrow involvement, bulky disease, or the involvement of extralymphatic organ or sites.

Often, the patients which will most benefit from the disclosed therapeutic methods are those patients who are refractory to other types of treatments, or who have relapsed following other types of treatments, such as chemotherapy or radiotherapy. However, the monoclonal antibody treatments disclosed in the present invention will be beneficial also to newly diagnosed patients, and may have a synergistic effect in decreasing the chance of relapse if administered in conjunction with other conventional therapies.

For instance, the methods of the present invention include methods comprising the administration of both monoclonal antibodies (or fragments thereof) to CD20 along with a chemotherapeutic regimen. Depending on the particular patient, said chemotherapy may be administered simultaneously or sequentially in either order. "Simultaneously" means either concurrently or during the same time period such that the circulating half-lives of the therapeutic agents overlaps.

Chemotherapeutic regimens which may be combined with the antibody treatments of the present invention include CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA with or without subsequent G-CSF treatment), VAD, M & P, C-Weekly, ABCM, MOPP and DHAP. The most preferred chemotherapeutic regimen is CHOP.

The primary anti-CD20 antibodies of the present invention are preferably human antibodies, or chimeric or humanized antibodies which are engineered with human constant region domains, such that the antibodies are able to stimulate human effector functions. A preferred antibody to be used in the methods of the present invention is RITUXAN® rituximab (IDEC Pharmaceuticals, Inc.).

Rituximab is one of a new generation of monoclonal antibodies developed to overcome limitations encountered with murine antibodies, including short half-life, limited ability to stimulate human effector functions, and immunogenicity. Rituximab is a genetically engineered monoclonal antibody with murine light- and heavy-chain variable regions and human gamma I heavy-chain and kappa light-chain constant regions. The chimeric antibody is composed of two heavy chains of 451 amino acids and two light chains of 213 amino acids and has an approximate molecular weight of 145 kD.

Rituximab is more effective than its murine parent in fixing complement and mediating ADCC, and it mediates CDC in the presence of human complement. The antibody inhibits cell growth in the B-cell lines FL-18, Ramos, and Raji, sensitizes chemoresistant human lymphoma cell lines to diphtheria toxin, ricin, CDDP, doxorubicin, and etoposide, and induces apoptosis in the DHL-4 human B-cell lymphoma line in a dose-dependent manner. In humans, the half-life of the antibody is approximately 60 hours after the first infusion and increases with each dose to 174 hours after the fourth infusion. The immunogenicity of the antibody is low; of 355 patients in seven clinical studies, only three (<1%) had a detectable anti-chimeric antibody (HACA) response.

The methods of the present invention may comprise administration of a radiolabeled antibody which binds to a protein on the surface of cancerous B cells. Such radiolabeled antibodies are preferably administered following administration of the human, chimeric or humanized antibody, which will decrease the amount of cancerous B cells in the bone marrow and lessen the likelihood of unwanted myeloablative suppression due to antibody binding to tumor cells in the marrow. Moreover, while CD20 is an ideal target for the immunotherapy of the present invention, it is possible that radiolabeled antibodies directed to other B cell surface antigens may also be used in the methods of the present invention. In particularly preferred embodiments, the radiolabeled antibodies are used in conjunction with unlabeled antibodies.

Approximately 80% of non-Hodgkin's lymphomas are B-cell-malignancies and >95% of these express the CD20 antigen on the cell surface. This antigen is an attractive target for immunotherapy because it is found exclusively on B cells, and not on hematopoietic stem cells, pro-B cells, normal plasma cells, or other normal tissues. It is not shed from the cell surface and does not modulate upon antibody binding.

The radiolabeled antibodies of the present invention may be labeled with any alpha or beta emitting radioisotope. However, a preferred isotope is $^{90}$Y, and a preferred antibody is Y2B8. Y2B8 was engineered from the same murine antibody, 2B8, as was rituximab. The 2B8 antibody has also been conjugated to different radiolabels for diagnostic and therapeutic purposes. To this end, copending applications Ser. Nos. 08/475,813, 08/475,815 and 08/478,967, herein incorporated by reference in their entirety, disclose radiolabeled anti-CD20 conjugates for diagnostic "imaging" of B cell lymphoma tumors before administration of therapeutic antibody. For instance, the "In2B8" conjugate comprises the murine monoclonal antibody, 2B8, attached to Indium[111] ($^{111}$In) (via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. Indium-[111] is selected as a diagnostic radionuclide because it emits gamma radiation and finds prior usage as an imaging agent.

Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, and 5,124,471 of Gansow also relate to polysubstituted DTPA chelates. These patents are incorporated herein in their entirety.

The specific bifunctional chelator used to facilitate chelation in applications Ser. Nos. 08/475,813, 08/475,815 and 08/478,967 was selected as it possesses high affinity for trivalent metals, and provides for increased tumor-to-non-tumor ratios, decreased bone uptake, and greater in vivo retention of radionuclide at target sites, i.e., B-cell lymphoma tumor sites. However, other bifunctional chelators are known in the art and may also be beneficial in tumor therapy.

Also disclosed in applications Ser. Nos. 08/475,813, 08/475,815 and 08/478,967 are radiolabeled therapeutic antibodies for the targeting and destruction of B cell lymphomas and tumor cells. In particular, the Y2B8 conjugate comprises the same anti-human CD20 murine monoclonal antibody, 2B8, attached to yttrium-[90] ($^{90}Y$) via the same bifunctional chelator. This radionuclide was selected for therapy for several reasons. The 64 hour half-life of $^{90}Y$ is long enough to allow antibody accumulation by the tumor and, unlike e.g. $^{131}I$, it is a pure beta emitter of high energy with no accompanying gamma irradiation in its decay, with a range of 100 to 1000 cell diameters. The minimal amount of penetrating radiation allows for outpatient administration of $^{90}Y$-labeled antibodies. Furthermore, internalization of labeled antibodies is not required for cell killing, and the local emission of ionizing radiation should be lethal for adjacent tumor cells lacking the target antigen.

Because the $^{90}Y$ radionuclide was attached to the 2B8 antibody using the same bifunctional chelator molecule MX-DTPA, the Y288 conjugate possesses the same advantages discussed above, e.g., increased retention of radionuclide at a target site (tumor). However, unlike $^{111}In$, it cannot be used for imaging purposes due to the lack of gamma radiation associated therewith. Thus, a diagnostic "imaging" radionuclide, such as $^{111}In$, can be used for determining the location and relative size of a tumor prior to and/or following administration of therapeutic chimeric or $^{90}Y$-labeled antibodies in the combined regimens of the invention. Additionally, indium-labeled antibody enables dosimetric assessment to be made.

Depending on the intended use of the antibody, i.e., as a diagnostic or therapeutic reagent, other radiolabels are known in the art and have been used for similar purposes. For instance, radionuclides which have been used in clinical diagnosis include $^{131}I$, $^{125}I$, $^{123}I$, $^{99}Tc$, $^{67}Ga$, as well as $^{111}In$. Antibodies have also been labeled with a variety of radionuclides for potential use in targeted immunotherapy (Peirersz et al., 1987). The use of monoclonal antibody conjugates for the diagnosis and treatment of cancer. Immunol. Cell Biol. 65: 111-125). These radionuclides include $^{188}Re$ and $^{186}Re$ as well as $^{90}Y$, and to a lesser extent $^{199}Au$ and $^{67}Cu$. U.S. Pat. No. 5,460,785 provides a listing of such radioisotopes and is herein incorporated by reference.

As reported in copending applications Ser. Nos. 08/475,813, 08/475,815 and 08/478,967 administration of the radiolabeled Y2B8 conjugate, as well as unlabeled chimeric anti-CD20 antibody (rituximab), resulted in significant tumor reduction in mice harboring a B cell lymphoblastic tumor. Moreover, human clinical trials reported therein showed significant B cell depletion in low-grade NHL lymphoma patients infused with rituximab. In fact, rituximab has recently been heralded the nation's first FDA-approved anti-cancer monoclonal antibody.

In addition, U.S. application Ser. No. 08/475,813, herein incorporated by reference, discloses sequential administration of RITUXANO® (rituximab), a chimeric anti-CD20, with both or either indium-labeled or yttrium-labeled murine monoclonal antibody for the treatment of low-grade NHL.

Although the radiolabeled antibodies used in these combined therapies are murine antibodies, initial treatment with chimeric anti-CD20 sufficiently depletes the B cell population such that the HAMA response is decreased, thereby facilitating a combined therapeutic and diagnostic regimen. Moreover, it was shown in U.S. application Ser. No. 08/475,813 that a therapeutically effective dosage of the yttrium-labeled anti-CD20 antibody following administration of rituximab is sufficient to (a) clear any remaining peripheral blood B cells not cleared by the chimeric anti-CD20 antibody; (b) begin B cell depletion from lymph nodes; or (c) begin B cell depletion from other tissues.

Autologous bone marrow transplantation is often a successful accompaniment to myeloablative therapy in helping to restore the immune system to patients who have undergone radiotherapy or chemotherapy. However, as discussed above, the patients who will benefit by the methods disclosed herein will often have lymphoma accompanied by bone marrow involvement. For such patients, there are often too many cancerous cells in the marrow to perform autologous transplantation.

When there is bone marrow involvement accompanying the intermediate- or high-grade lymphoma, such patients may benefit by prior treatment with human, chimeric or humanized anti-CD20 antibody before bone marrow harvesting in order to decrease the quantity of tumor cells in the bone marrow or stem cell preparation. In fact, rituximab can be administered at induction, in vivo purging, mobilization, conditioning, post-transplant reinfusion and at any other time during bone marrow or stem cell transplant for the purpose of improving the survival rate of transplant recipients. "Induction" is meant to refer to the initial therapies aimed at achieving induction of remission. Typically, induction involves the administration of some type of chemotherapy, i.e., CHOP.

The phrase "in vivo purging" is meant to refer to treatment particularly geared toward purging tumor cells from the bone marrow within the patient, although certainly such treatment might be beneficial for tumor cells in the peripheral blood and at other sites as well. Such a step may precede the harvest of bone marrow as a means of decreasing the number of tumor cells therein. Rituximab and other chimeric lymphoma cell-depleting antibodies provide an advantage in this regard over radiolabeled antibodies in that they may be used to purge the bone marrow of cancerous cells without damaging healthy progenitors.

"Mobilization" refers to the process by which stem cells are mobilized to leave the bone marrow and enter the circulatory system, and provides an alternative to bone marrow harvest per se as a source of stem cells for transplantation. Mobilization is typically achieved by administering a short burst of chemotherapy and/or growth factors. The growth factor G-CSF is commonly used, but others may be used according to the knowledge of the skilled artisan.

Typically, during mobilization, stem cells are separated from blood (which is then put back into the patient), and the stem cells are frozen until the patient is ready to be reinfused. Ex vivo purging with rituximab, or other antibodies known in the art to be useful for this purpose, may then be used to deplete tumor cells in the stem cell preparation.

Conditioning" refers to a process by which the patient is prepared to receive the autologous bone marrow reinfusion or allogeneic transplant. This is typically accomplished with a very high dose of chemotherapy in order to deplete all bone marrow cells, i.e., both healthy cells and tumor cells, from the bone marrow. Chemotherapeutic drugs that may be given at sufficiently high doses without risking the patient's life, e.g. cyclophosphamide, are known in the art.

Thus, with rituximab treatment at the various stages of transplantation, marrow may be harvested prior to myeloablative radiotherapy, and reintroduced subsequent to such therapy with less concern about reintroducing tumor cells originally harvested with the marrow back into the patient. Of course, the patient may then benefit by additional or subsequent treatment with chimeric anti-CD20 antibody as part of a maintenance regimen, or by administration of a radiolabeled antibody such as Y2B8 to further decrease the chance of relapse.

The methods of the present invention also encompass combined therapy comprising administration of at least one cytokine along with an anti-CD20 antibody or fragment thereof. Such a cytokine may be administered simultaneously or sequentially in any order. In particular, cytokines may be useful in upregulating the expression of CD20 on the surface of cancerous B cells prior to administration of the anti-CD20 antibody. Cytokines useful for this purpose include IL-4, GM-CSF and TNF-alpha, and possibly others.

Cytokines may also be administered simultaneously or within the same time frame in order to increase or control certain effector functions mediated by the therapeutic antibody. Cytokines useful for this purpose include interferon alpha, G-CSF and GM-CSF, and possibly others.

Preferred dosage regimens and exemplary embodiments will now be illustrated by way of the following data.

Single-Agent Studies

In a study conducted in Europe and Australia, alternative dosing schedules were evaluated in 54 relapsed or refractory intermediate- or high-grade NHL patients (Coiffier B, Haioun C, Ketterer N, Engert A, Tilly H, Ma D, Johnson P, Lister A, Feuring-Buske M, Radford J A, Capdeville R, Diehl V, Reyes F. Rituximab (anti-CD20 monoclonal antibody) for the treatment of patients with relapsing or refractory aggressive lymphoma: a multicenter phase H study. *Blood* 1998; 92:1927-1932).

Rituximab was infused at 375 mg/m2 weekly for 8 doses or at 375 mg/m2 once followed by 500 mg/m2 weekly for 7 doses. The ORR was 31%; (CR 9%, PR 22%) no significant difference between the dosing regimens was observed. Patients with diffuse large-cell lymphoma (N=30) had an ORR of 37% and those with mantle-cell lymphoma (N=12) had an ORR of 33%.

Treatment of Bulky Disease

Contrary to early assumptions about antibody therapy being useful only in micrometastatic disease, rituximab is quite active in high bulk disease. In a separate study, 31 patients with relapsed or refractory, bulky low-grade NHL (single lesion of >10 cm in diameter) received 375 mg/m$^2$ rituximab as four weekly infusions. Twelve of 28 evaluable patients (43%) demonstrated a CR (1, 4%) or PR (11, 39%) (Davis T, White C, Grillo-López A, Velasquez W, Link B, Maloney D, Dillman R, Williams M, Mohrbacher A, Weaver R, Dowden S, Levy R. Rituximab: First report of a Phase II (PII) trial in NHL patients (pts) with bulky disease. *Blood* 1998; 92 (10 Suppl 1):414a).

This suggests that with the appropriate dosages depending on the extent of disease and the number of circulating tumor cells (i.e., such as the increased dosages described above), rituximab therapy will also be useful for more aggressive intermediate- or high-grade NHLs accompanied by bulky disease.

Combination of Rituximab and CHOP Chemotherapy

In another study, 31 patients with intermediate- or high-grade NHL (19 females, 12 males, median age 49) received rituximab on Day 1 of each of six 21-day cycles of CHOP: Link B, Grossbard M, Fisher R, Czuczman M, Gilman P, Lowe A, Vose J. Phase II pilot study of the safety and efficacy of rituximab in combination with CHOP chemotherapy in patients with previously untreated- or high-grade NHL. *Proceedings of the American Society of Clinical Oncology* 1998; 17:3a). Of 30 evaluable patients, there were 19 CR (63%) and 10 PR (33%), for an ORR of 96%. This regimen was considered well tolerated and may result in higher response rates than with rituximab or CHOP alone.

The NCI Division of Cancer Treatment and Diagnosis is collaborating with IDEC Pharmaceuticals Corporation to explore rituximab treatment in other indications. A Phase II trial of CHOP versus CHOP and rituximab is being conducted by ECOG, CALGB, and SWOG in older patients (>60 years) with mixed, diffuse large cell, and immunoblastic large cell histology NHL (N=630 planned). This study includes a secondary randomization to maintenance with rituximab versus nonmaintenance.

A Phase III trial of rituximab and CHOP in 40 patients with previously untreated mantle-cell lymphoma is also ongoing at the Dana Farber Institute. Rituximab is administered on Day 1 and CHOP is given on Days 1-3 every 21 days for 6 cycles. Accrual for this study has been completed. A Phase II trial of CHOP followed by rituximab in newly diagnosed follicular lymphoma conducted by SWOG has also been completed. Results of these two trials are being analyzed.

A Phase II trial of CHOP and rituximab versus CHOP alone in HIV-related NHL conducted by the AIDS Malignancy Consortium is ongoing; 120 patients are planned.

Rituximab after Myeloablative Therapy Relapse

Rituximab has shown promising early results in patients with relapsed intermediate-grade NHL after high-dose therapy with autologous PBSC support. Six of seven patients responded (1 CR and 5 PR) and one patient had stable disease; therapy was well tolerated (Tsai, D, Moore H, Porter D, Vaughn D, Luger S, Loh R, Schuster S, Stadtmauer E. Progressive intermediate grade non-Hodgkin's lymphoma after high dose therapy and autologous peripheral stem cell transplantation (PSCT) has a high response rate to rituximab. *Blood* 1998; 92:415a, #1713).

The invention claimed is:

1. A method of treating a >60 year old diffuse large cell lymphoma patient comprising administering anti-CD20 antibody and CHOP (cyclophosphamide, hydroxydaunorubicin/doxorubicin, vincristine, and prednisone/prednisolone) chemotherapy to the patient, wherein the anti-CD20 antibody is administered to the patient in combination with a transplantation regimen.

2. The method of claim 1, wherein the antibody comprises a chimeric anti-CD20 antibody.

3. The method of claim 2, wherein the antibody comprises rituximab.

4. The method of claim 1, wherein the lymphoma is accompanied by bone marrow involvement.

5. The method of claim 1, wherein the transplantation regimen comprises bone marrow transplantation.

6. The method of claim 1, wherein the anti-CD20 antibody and CHOP are administered simultaneously.

7. The method of claim 6, wherein the anti-CD20 antibody and CHOP are administered concurrently.

8. The method of claim 7, wherein the antibody comprises rituximab.

9. The method of claim 6, comprising administering the anti-CD20 antibody on Day 1 of each chemotherapy cycle and the CHOP on Day 1 of each chemotherapy cycle.

10. The method of claim 9, wherein the antibody comprises rituximab.

11. A method of treating a patient with diffuse large cell lymphoma comprising administering rituximab and CHOP (cyclophosphamide, hydroxydaunorubicin/doxorubicin, vincristine, and prednisone/prednisolone) chemotherapy to the patient, wherein the patient is >60 years old and wherein the rituximab and the CHOP are administered concurrently.

12. A method of treating a >60 year old diffuse large cell lymphoma patient comprising administering rituximab and CHOP (cyclophosphamide, hydroxydaunorubicin/doxorubicin, vincristine, and prednisone/prednisolone) chemotherapy to the patient, wherein the rituximab is administered on Day 1 of each chemotherapy cycle and the CHOP is administered on Day 1 of each chemotherapy cycle.

13. The method of claim 9 comprising administering six or eight chemotherapy cycles, wherein in each chemotherapy cycle a 375 mg/m$^2$ dose of the anti-CD20 antibody is administered to the patient.

14. The method of claim 13 comprising administering eight chemotherapy cycles, wherein in each chemotherapy cycle a 375 mg/m$^2$ dose of the anti-CD20 antibody is administered to the patient.

15. The method of claim 12 comprising administering six or eight chemotherapy cycles, wherein in each chemotherapy cycle a 375 mg/m$^2$ dose of rituximab is administered to the patient.

16. The method of claim 15 comprising administering eight chemotherapy cycles, wherein in each chemotherapy cycle a 375 mg/m$^2$ dose of rituximab is administered to the patient.

\* \* \* \* \*